United States Patent [19]
Scovil et al.

[11] Patent Number: 5,588,442
[45] Date of Patent: Dec. 31, 1996

[54] SHAFT MOVEMENT CONTROL APPARATUS AND METHOD

[75] Inventors: Brian Scovil, New Hope; Todd A. Berg, Lino Lakes; Kevin Klitz, Plymouth; Thomas J. Bachinski, Lakeville; John W. Humphrey, Eden Prairie; Scott Thome, Waite Park; Roger Hastings, Maple Grove, all of Minn.

[73] Assignee: SciMed Life Systems, Inc., Maple Grove, Minn.

[21] Appl. No.: 397,578

[22] Filed: Mar. 2, 1995

Related U.S. Application Data

[63] Continuation-in-part of Ser. No. 48,492, Apr. 16, 1993, Pat. No. 5,555,893, which is a continuation-in-part of Ser. No. 929,083, Aug. 12, 1992.

[51] Int. Cl.$^6$ .................................................. A61B 5/00
[52] U.S. Cl. ............................................ 128/772; 128/657
[58] Field of Search ....................................... 128/657, 658, 128/772; 604/95, 164, 280–283

[56] References Cited

U.S. PATENT DOCUMENTS

| | | | |
|---|---|---|---|
| 3,358,676 | 12/1967 | Frei et al. | 128/1.3 |
| 3,674,014 | 7/1972 | Tillander | 128/2.05 R |
| 3,722,505 | 3/1973 | Kolin | 128/2.05 F |
| 3,941,119 | 3/1976 | Corrales | 128/2 M |
| 3,961,632 | 6/1976 | Moossun | 128/347 |
| 4,054,128 | 10/1977 | Seufert et al. | 128/4 |
| 4,077,412 | 3/1978 | Moosun | 128/347 |
| 4,134,405 | 1/1979 | Smit | 128/303 R |
| 4,162,679 | 7/1979 | Reenstierna | 128/419 P |
| 4,244,362 | 1/1981 | Anderson | 128/200.26 |
| 4,249,536 | 2/1981 | Vega | 128/349 B |
| 4,315,509 | 2/1982 | Smit | 128/303 R |
| 4,616,648 | 10/1986 | Simpson | 128/303 R |
| 4,671,287 | 6/1987 | Fiddian-Green | 128/631 |
| 4,726,369 | 2/1988 | Mar | 128/303 R |
| 4,762,129 | 8/1988 | Bonzel | 128/344 |
| 4,784,117 | 11/1988 | Miyazaki | 128/4 |
| 4,784,646 | 11/1988 | Feingold | 604/175 |

(List continued on next page.)

FOREIGN PATENT DOCUMENTS

| | | |
|---|---|---|
| 0416734A1 | 7/1990 | European Pat. Off. . |
| 0415332A1 | 8/1990 | European Pat. Off. . |
| 0409372A1 | 1/1991 | European Pat. Off. . |
| 0232968B1 | 9/1992 | European Pat. Off. . |
| 2245495 | 1/1992 | United Kingdom . |
| WO81/02109 | 8/1981 | WIPO . |
| WO89/07958 | 9/1989 | WIPO . |
| WO93/15786 | 8/1993 | WIPO . |
| WO94/03229 | 2/1994 | WIPO . |

OTHER PUBLICATIONS

J. Driller, M. Casarella, T. Asch, S. K. Hilal; *The POD Bronchial Catheter*, IEEE Transactions on Magnetics, vol. Mag–6, No. 2, pp. 353–355, Jun. 1970.

A. Snider; *New Techniques Used in Lung Biopsy*, The Washington Post, p. E16, Thursday, Dec. 4, 1969.

D. Montgomery and R. Weegal; *Magnetic Forces for Medical Applications*, IEEE Transactions on Magnetics, p. 374, Jun. 1970.

D. Montgomery, J. Hale, N. Pierce and S. Yodh; *A Magnetically Guided Catheter System for Intracranial Use in Man*, IEEE Transactions on Magnetics, pp. 374–375, Jun. 1970.

H. Tillander; *Selective Angiography with a Catheter Guided by a Magnet*, IEEE Transactions on Magnetics, vol. Mag–6, No. 2, pp. 355–358, Jun. 1970.

*Primary Examiner*—Max Hindenburg
*Attorney, Agent, or Firm*—Nawrocki, Rooney & Silvertson, P.A.

[57] ABSTRACT

Guide catheter exchange device and method of exchanging a guide catheter. The guide catheter exchange device includes a magnetically responsive segment located on a proximal end for maintaining a previously placed guide wire in position across a stenosis, while performing a guide catheter exchange procedure. The guide catheter exchange device allows a guide catheter exchange procedure to be performed by a solo physician.

36 Claims, 26 Drawing Sheets

U.S. PATENT DOCUMENTS

| | | | |
|---|---|---|---|
| 4,790,809 | 12/1988 | Kuntz | 604/8 |
| 4,804,054 | 2/1989 | Howson et al. | 128/898 |
| 4,809,713 | 3/1989 | Grayzel | 128/785 |
| 4,829,999 | 5/1989 | Auth | 128/303 R |
| 4,860,742 | 8/1989 | Park et al. | 128/303 R |
| 4,875,489 | 10/1989 | Messner et al. | 128/772 |
| 4,922,923 | 5/1990 | Gambale et al. | 128/772 |
| 4,932,413 | 6/1990 | Shockey et al. | 128/657 |
| 4,944,740 | 7/1990 | Buchbinder et al. | 606/194 |
| 4,947,864 | 8/1990 | Shockey et al. | 128/772 |
| 4,976,689 | 12/1990 | Buchbinder et al. | 604/95 |
| 5,020,367 | 6/1991 | White | 73/319 |
| 5,035,686 | 7/1991 | Crittenden et al. | 604/96 |
| 5,040,548 | 8/1991 | Yock | 128/898 |
| 5,061,273 | 10/1991 | Yock | 606/194 |
| 5,117,838 | 6/1992 | Palmer et al. | 128/772 |
| 5,120,323 | 6/1992 | Shockey et al. | 604/282 |
| 5,156,594 | 10/1992 | Keith | 604/96 |
| 5,161,534 | 11/1992 | Berthiaume | 128/657 |
| 5,195,535 | 3/1993 | Shank | 128/772 |
| 5,234,407 | 8/1993 | Teirstein et al. | 604/53 |
| 5,255,690 | 10/1993 | Keith et al. | 128/772 |
| 5,257,636 | 11/1993 | White | 128/897 |
| 5,267,958 | 12/1993 | Buchbinder et al. | 604/96 |
| 5,269,759 | 12/1993 | Hernandez et al. | 604/96 |
| 5,281,203 | 1/1994 | Ressemann | 604/164 |
| 5,282,478 | 2/1994 | Fleischhaker, Jr. et al. | 128/772 |
| 5,325,746 | 7/1994 | Anderson | 81/487 |
| 5,354,282 | 10/1994 | Bierman | 604/180 |
| 5,464,023 | 11/1995 | Viera | 128/772 |
| B1 4,762,129 | 8/1988 | Bonzel | 606/194 |

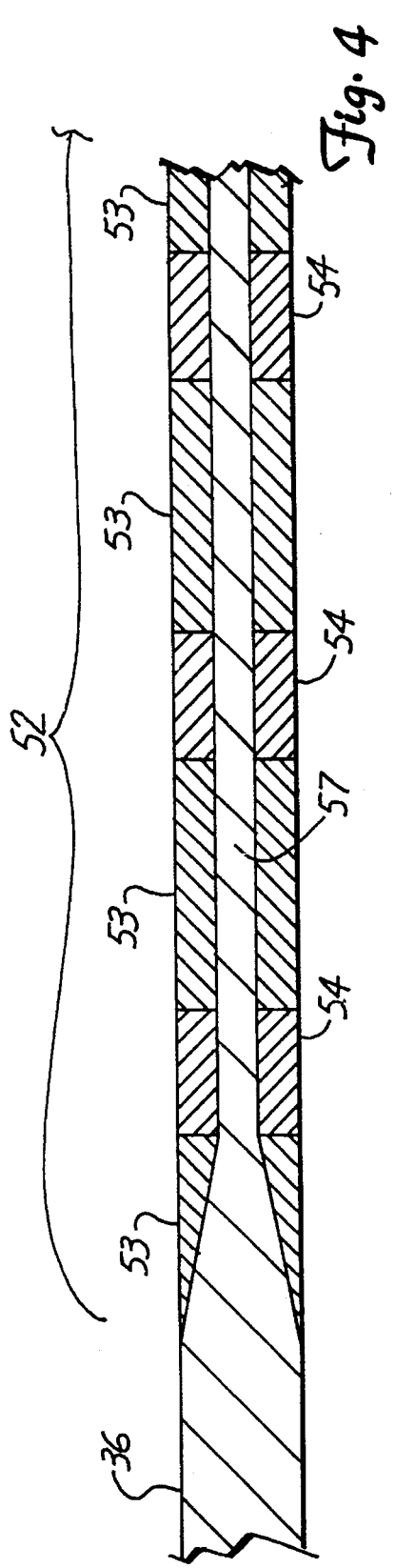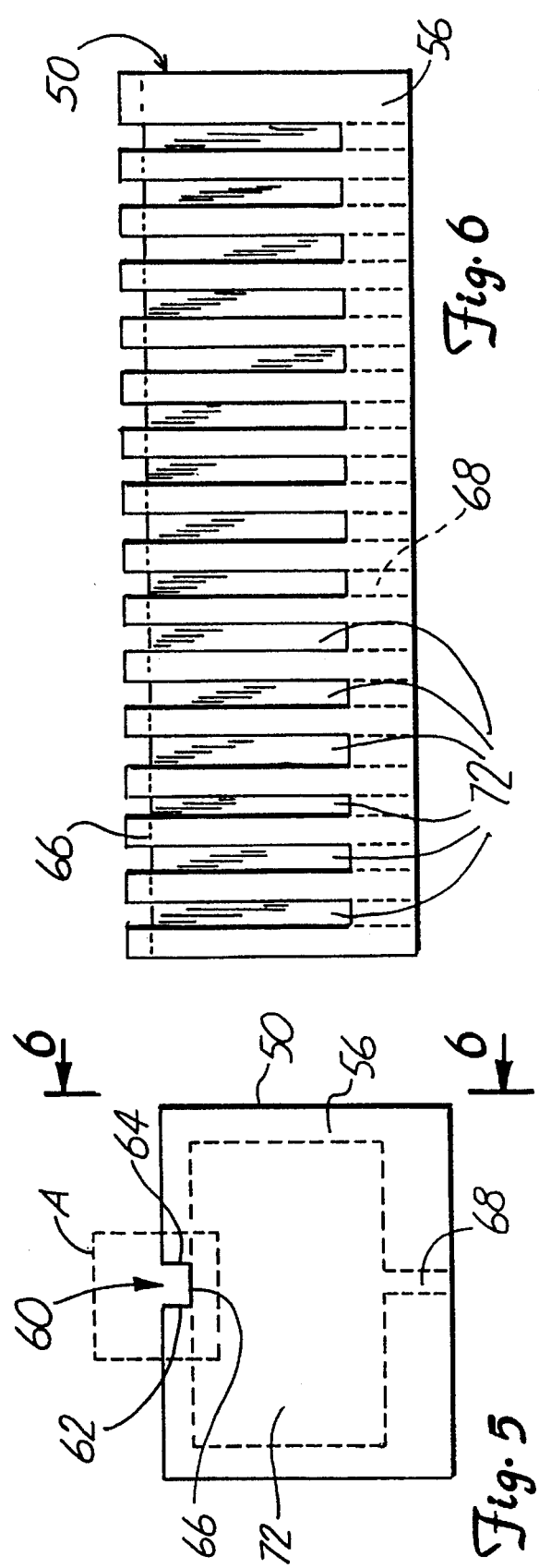

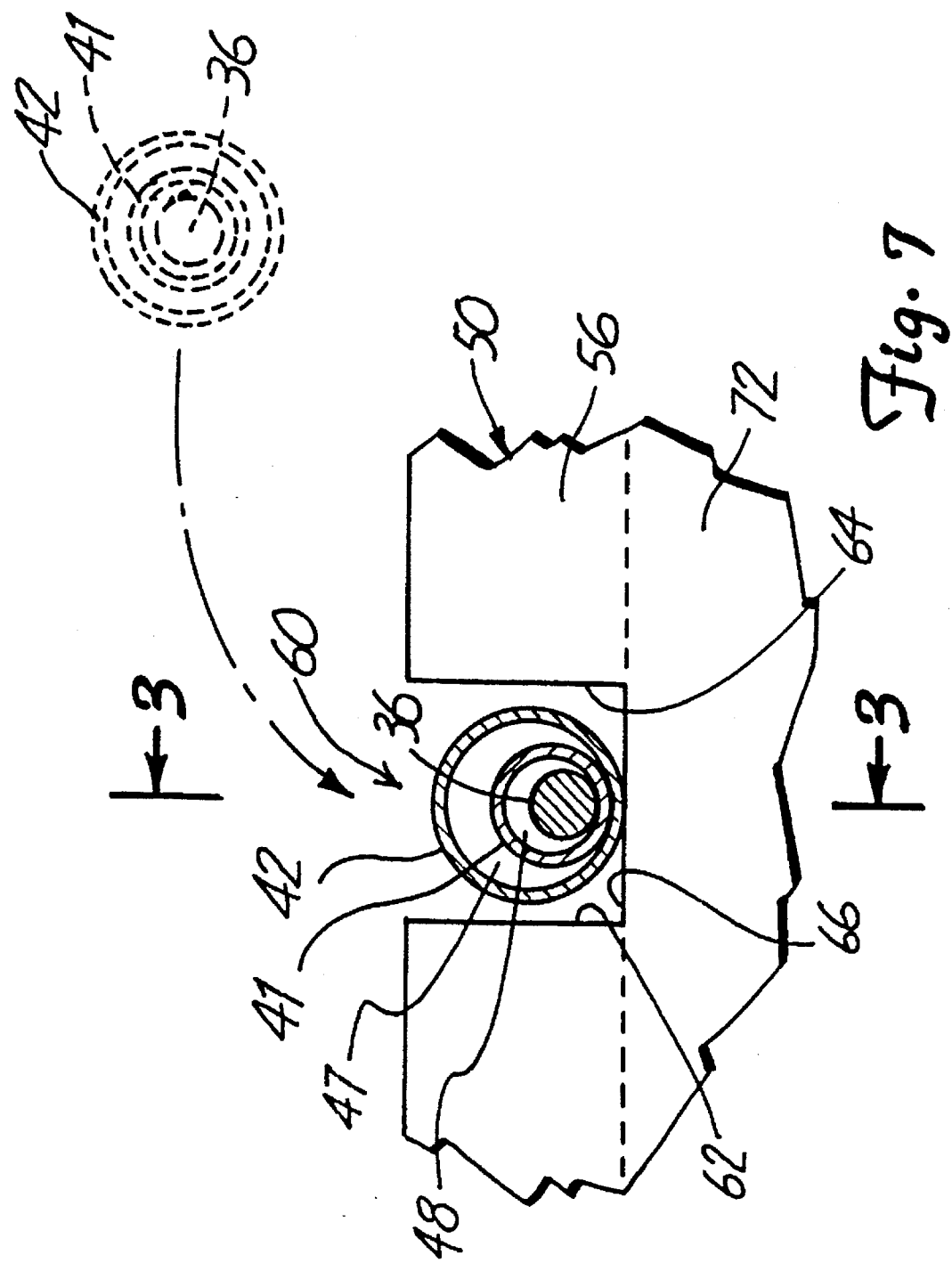

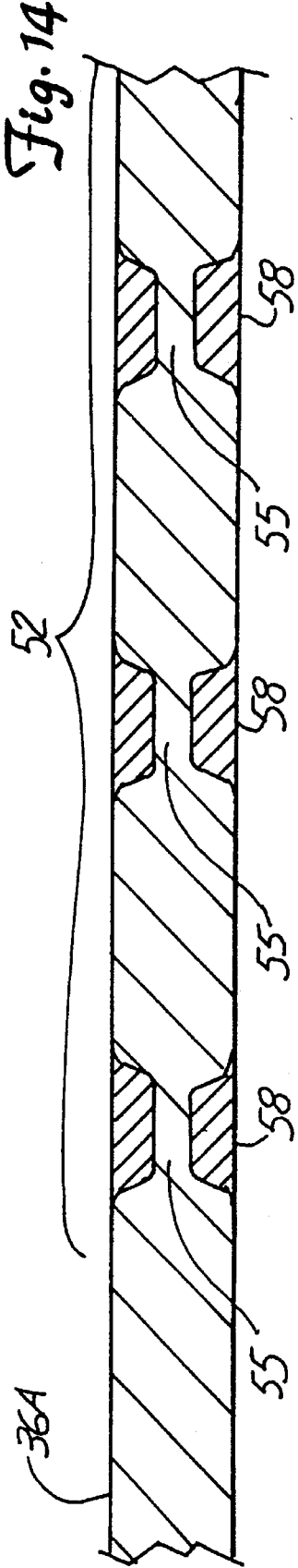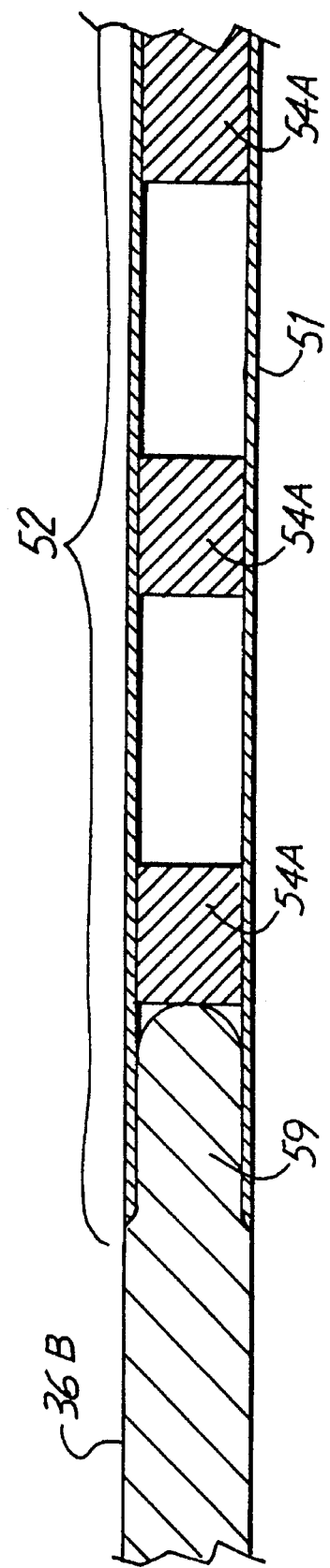

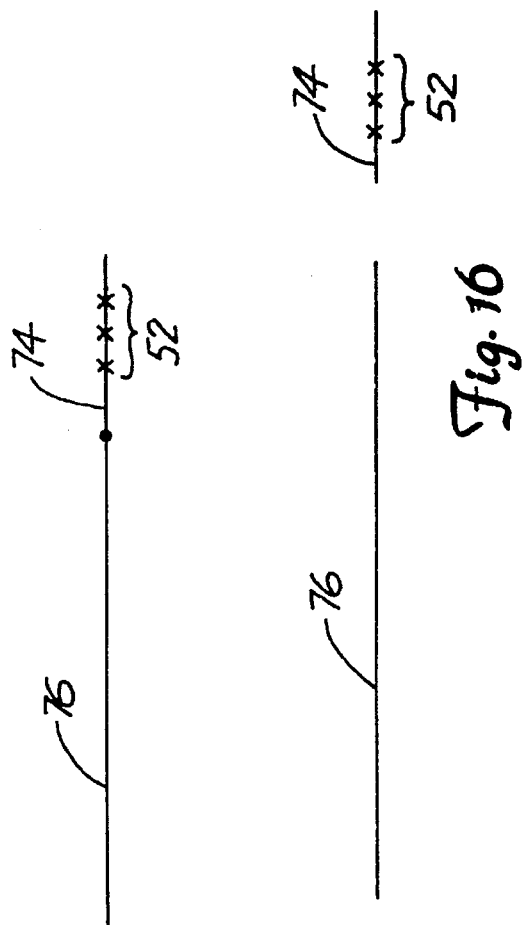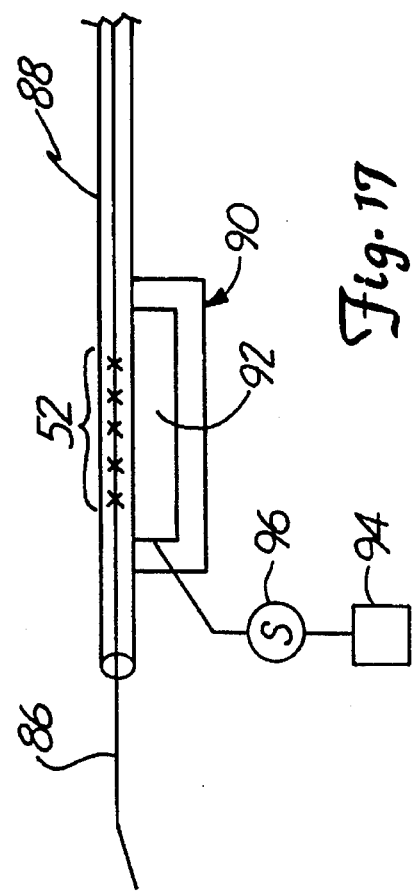

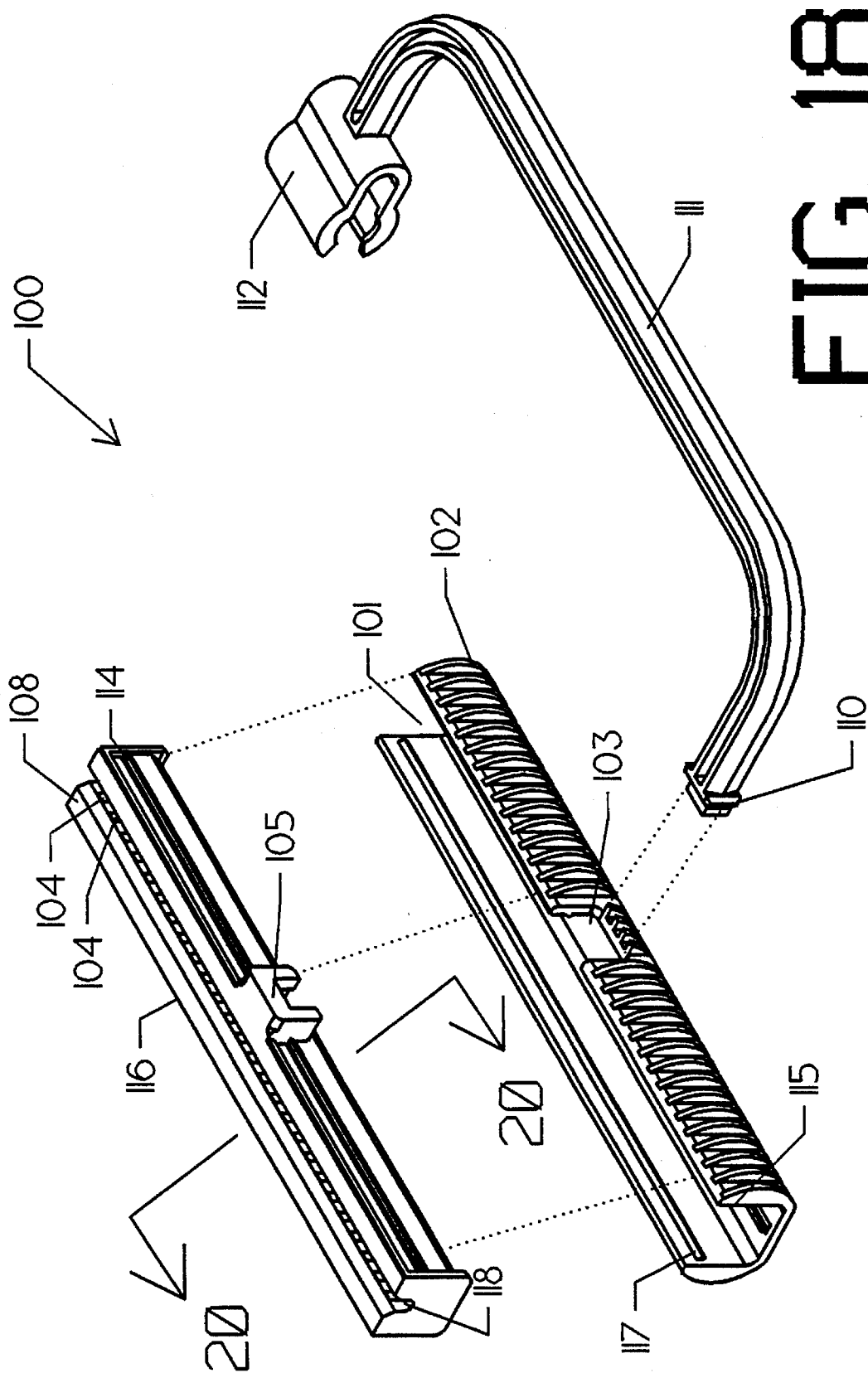

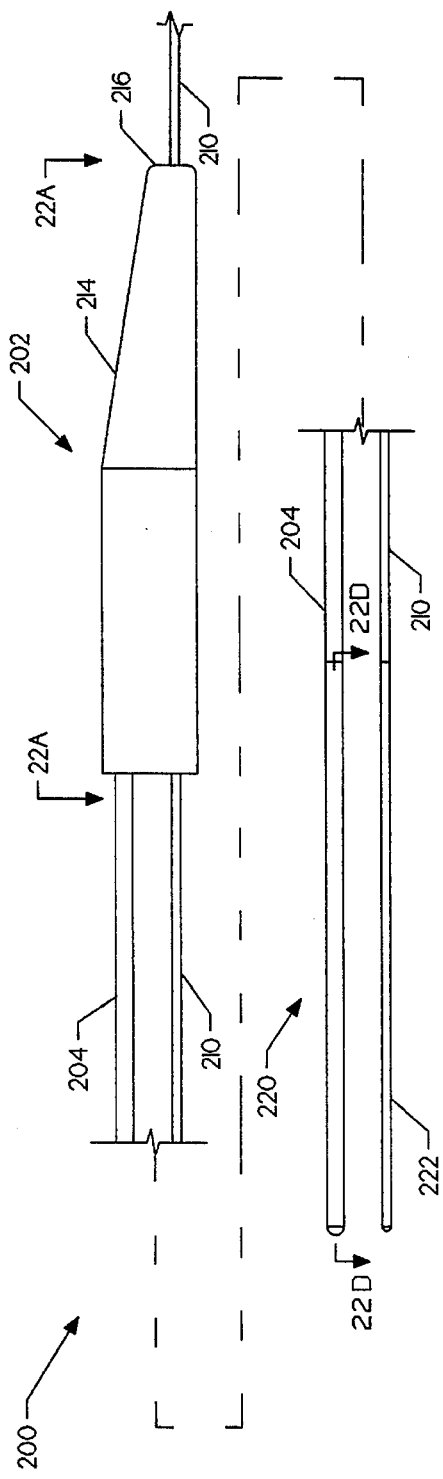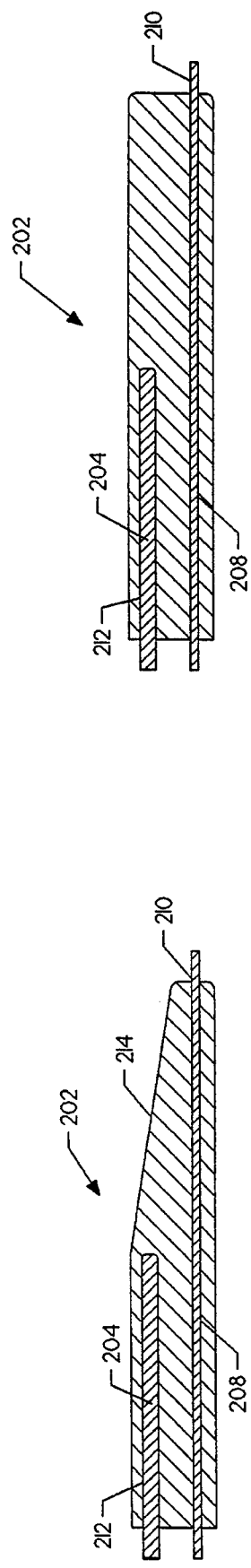

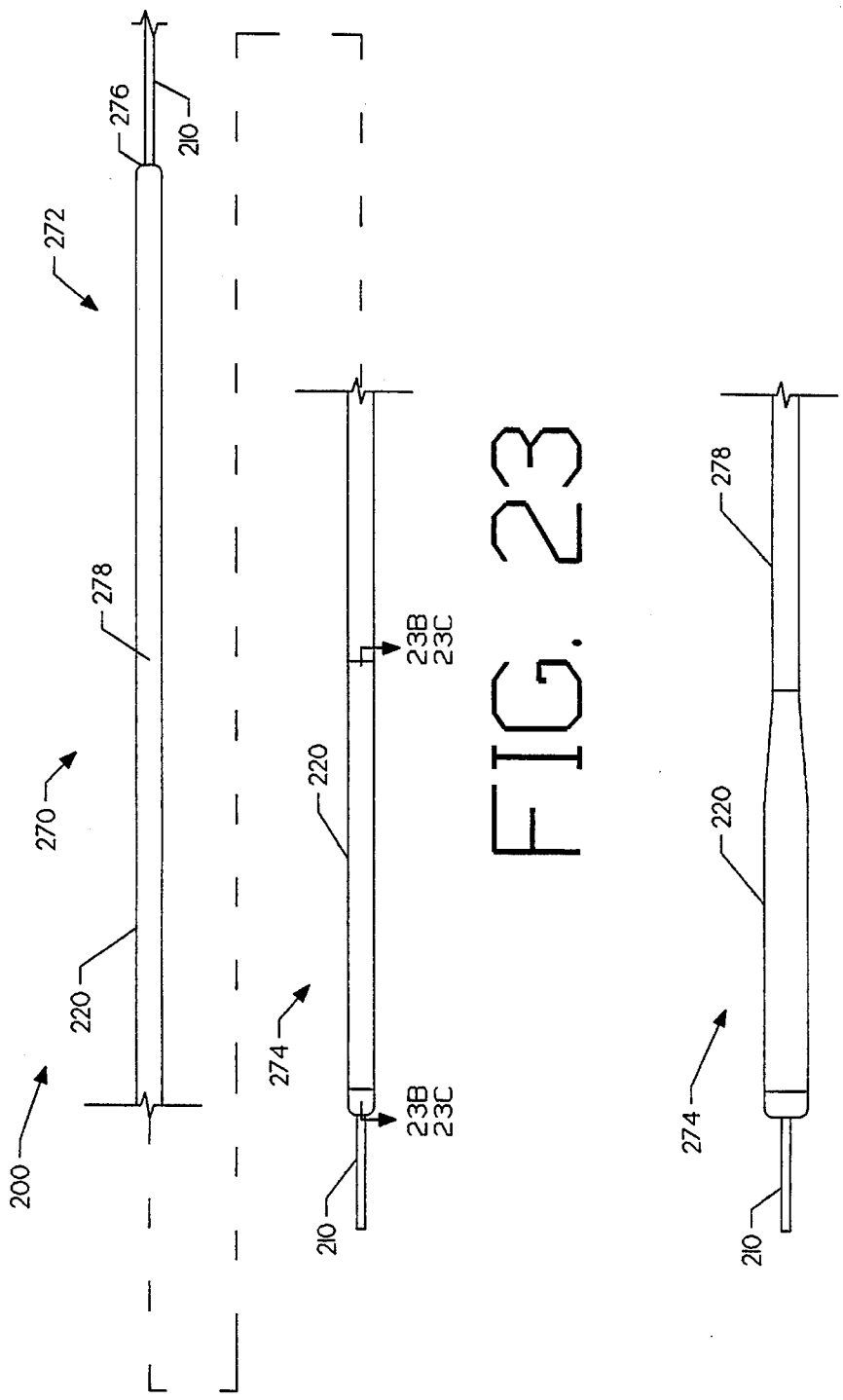

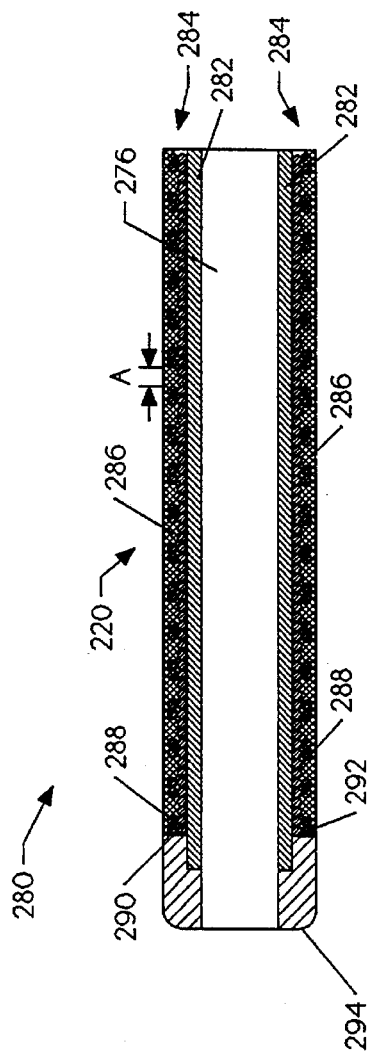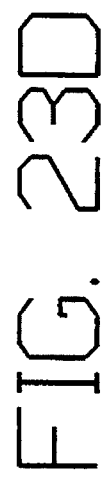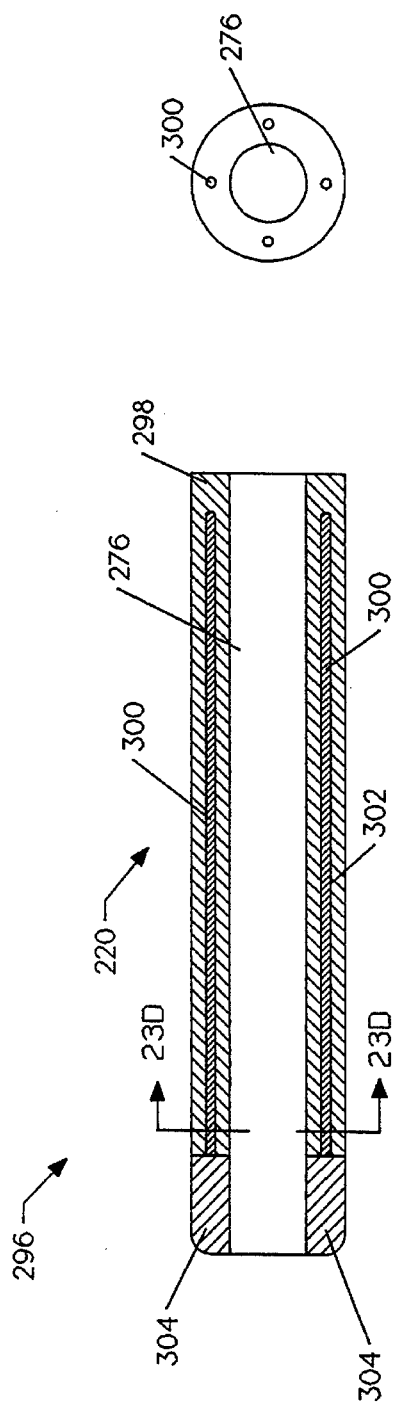

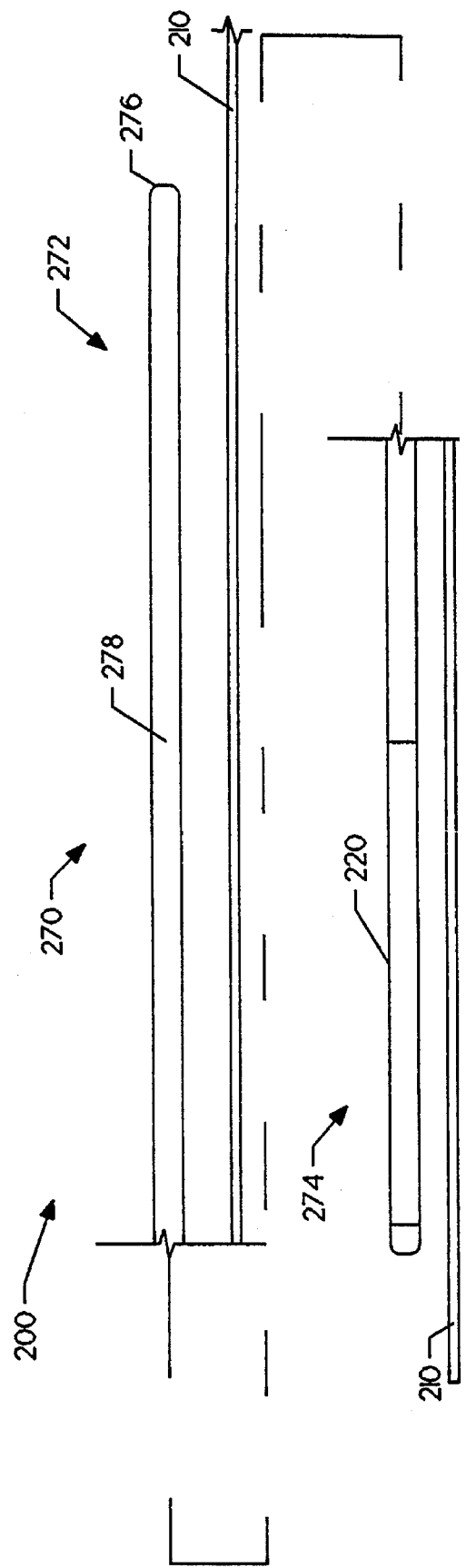

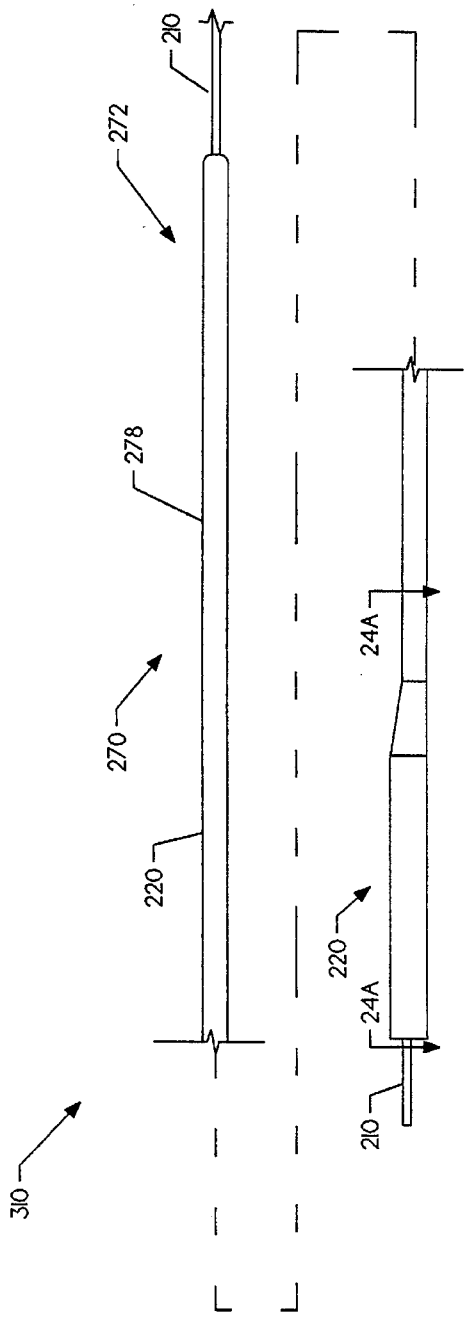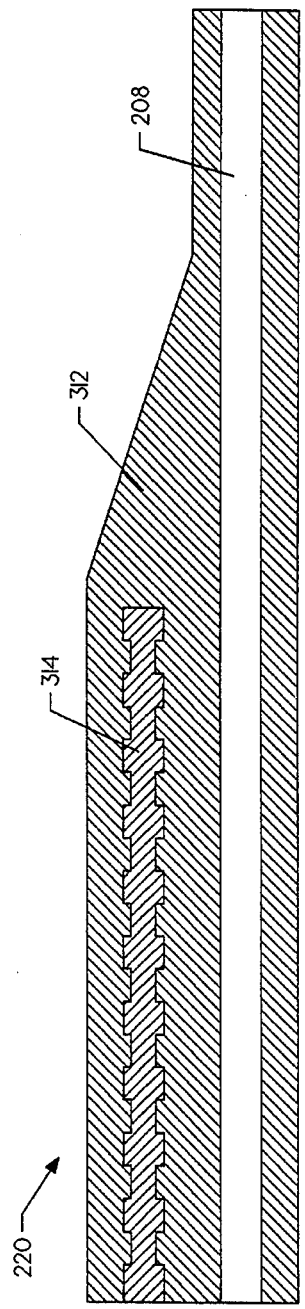

SHAFT MOVEMENT CONTROL APPARATUS AND METHOD

CROSS REFERENCES TO CO-PENDING APPLICATIONS

This application is a continuation-in-part of U.S. Pat. application Ser. No. 08/048,492, filed on Apr. 16, 1993, entitled "Shaft Movement Control Apparatus and Method", U.S. Pat. No. 5,555,893 which is a continuation-in-part of U.S. Ser. No. 07/929,083, filed Aug. 12, 1992.

BACKGROUND OF THE INVENTION

The present invention relates to the field of medical devices, particularly catheters. In particular, the present invention relates to a method and device for controlling movement of an elongate shaft for use in the catheterization of a patient, where a portion of the shaft is inserted within the patient.

Angioplasty has gained wide acceptance in recent years as an efficient and effective method for treating types of vascular diseases. In particular, angioplasty is widely used for opening stenoses in the coronary arteries, although it is also used for treatment of stenoses in other parts of the vascular system.

The most widely used form of angioplasty makes use of a dilatation catheter which has an inflatable balloon at its distal end. Using fluoroscopy, the physician guides the dilatation catheter through the vascular system until the balloon is positioned across the stenosis. The balloon is then inflated by supplying a fluid under pressure through an inflation lumen to the balloon. The inflation of the balloon causes stretching of the artery and pressing the lesion into the artery wall to re-establish acceptable blood flow through the artery. In some angioplasty procedures, it may be desirable to use a series of dilatation catheters having different sizes or balloon configurations.

One type of dilatation catheter has a guide lumen provided therein so that a guide wire can be used to establish the path through the stenosis. The dilatation catheter is then advanced over the guide wire until the balloon is positioned across the stenosis. The use of a guide wire enables the catheter to be advanced through the blood vessel relatively quickly, thereby reducing the time required for the procedure.

A "standard" guide wire for use in coronary angioplasty is about 175 cm long while a typical coronary angioplasty catheter is about 150 cm long. When the catheter is in place over the guide wire for use, a portion of the guide wire protrudes proximally from the catheter. The protruding portion enables the guide wire to be manipulated by a physician.

In some instances, it may be desirable to exchange one dilatation catheter (already on the guide wire) for a second dilatation catheter. It is usually preferred that the catheter be removed in a manner which enables the guide wire to remain in place in the blood vessel so that the succeeding catheter may be inserted into the blood vessel, over the guide wire already in place, and guided to the stenosis in the blood vessel. To maintain a guide wire in place while withdrawing the catheter, the guide wire must be gripped at its proximal end to prevent it from being pulled out of the blood vessel with the catheter. The catheter, however, is longer than the proximal portion of the guide wire which protrudes out the patient. Thus, before the catheter is fully withdrawn, it completely covers the proximally extending portion of the guide wire. As a result, there was no means by which a standard guide wire can be held in place to prevent it from being withdrawn together with the catheter. To withdraw the catheter while leaving the guide wire in place, a guide wire with a longer effective length was required.

One means for addressing this difficulty is to use an exchange wire when performing a catheter exchange. An exchange wire may be used initially or may be exchanged for a standard guide wire already in place in the patient. An exchange wire typically is much longer (e.g., 300 cm) than the typical or standard guide wire. The additional length of the exchange wire results in a proximally protruding portion which is longer than the length of the catheter to be removed. When a catheter is removed, some part of the proximally protruding portion of the exchange wire is always exposed to provide a means by which the exchange wire can be gripped and its position in the blood vessel maintained. The succeeding catheter is then inserted into the patient over the exchange wire.

It is generally recognized as undesirable to insert, advance and withdraw a series of guide wires during these types of procedures. Repeated guide wire insertions increase the risk of injury to the patient and also increase the time required for the procedure. It also requires exposure of the patient to additional radiation because of the additional fluoroscopy which is required to properly place the successive guide wires across the stenosis. In addition, long exchange wires are cumbersome and difficult to handle while maintaining the guide wire in place across the stenosis.

Techniques to eliminate the need to change guide wires have been proposed. One solution is the use of a guide wire extension which is attached to the proximal end of the guide wire while the guide wire remains in place in the patient. The guide wire extension effectively increases the length of the guide wire to that of an exchange guide wire. While the technique substantially shortens the duration of the procedure because the extension can be attached at the proximal end of the guide wire much faster than an exchange of guide wires can be performed, the extended guide wire is still cumbersome as the physician is required to handle an extended length of a guide wire outside of the patient during at least a portion of the procedure.

One means for catheter exchange without lengthening the guide wire is by use of a balloon catheter with a guide wire lumen located only adjacent the distal end of the catheter. With this configuration, the guide wire is external to the balloon catheter except adjacent the distal end of the balloon catheter. This catheter arrangement allows the catheter to be withdrawn over the guide wire without requiring the physician to completely release the guide wire until the distal end of the catheter is outside of the patient's body. The guide wire lumen on the catheter is shorter than the length of exposed guide wire, which allows at least some portion of the proximal end of the guide wire to be exposed at all times so that it can be grasped and its position relative to the stenosis can be maintained during removal of the catheter.

Another means for exchanging a catheter without the use of an extended guide wire is to engage the guide wire at a point distally of the catheter and hold it in place relative to the stenosis. This has been done by providing an inflatable guide wire holding balloon which is adapted to be inflated only within a guide catheter. In this arrangement, the dilatation catheter in the patient is withdrawn over the guide wire and inside of the guide catheter a short distance. The guide wire holding balloon is aligned distally relative to the dilatation catheter and is then inflated, thereby "trapping" the guide wire against an inner wall of the guide catheter (and constraining the guide wire from longitudinal movement relative to the guide catheter). The dilatation catheter is then withdrawn over the guide wire (the proximal end of the guide wire can be released) and a second dilatation catheter is placed on the guide wire and advanced along the guide wire to the point where the guide wire is trapped against the guide catheter wall. The guide wire holding balloon is then deflated and the physician advances the second dilatation catheter along the guide wire to the stenosis to continue the procedure. It also has been disclosed that mechanical means such as a wire snare be used within a guide catheter to secure the guide wire thereto, instead of a balloon.

While arrangements have been proposed to facilitate catheter exchanges in guide wire catheter systems without the need for a long guide wire length, they require a modified catheter (no full-length guide wire lumen) or additional components within the patient (e.g., balloon for trapping guide wire within guide catheter). It is desired to devise an arrangement which allows catheter exchanges over a standard length guide wire using a catheter having a full-length guide wire lumen.

SUMMARY OF THE INVENTION

The present invention is a method and device for controlling movement of a shaft for use in the catheterization of a patient where a distal portion of the shaft is inserted within the patient. The present invention is also useful for facilitating movement of a tube relative to a shaft extending through the tube, where distal portions of both the tube and the shaft are inserted within a patient.

The device of the present invention includes two pieces used in conjunction with each other. The first piece is an operative segment on the shaft. The second piece is an ancillary tool which, when positioned adjacent the operative segment on the shaft, cooperates with the operative segment to create a coupling force field between the operative segment and the tool, thus coupling the tool and the shaft together. The force created between the two pieces is strong enough to maintain the position of the shaft relative to the tool when the tube is aligned over the operative segment of the shaft.

In one preferred embodiment, the present invention is used to facilitate catheter exchanges in a guide wire catheter system without the need for a long guide wire length. In this preferred embodiment, the shaft is a guide wire, and the tube is a catheter with a lumen for slidably receiving the guide wire. The coupling force field between the operative segment on the guide wire and the tool is created by magnetism and is strong enough to maintain the tool and the guide wire is a coupled relation when the catheter is aligned over the operative segment on the guide wire and the catheter is moved longitudinally relative to the guide wire. The materials used to create the magnetic coupling force may be permanent magnets or magnetically permeable material.

The present invention is ideally suited for facilitating catheter exchanges without the need for a long guide wire length or a modified catheter. When a guide wire catheter system utilizing the present invention is pre-inserted within the vessel of a patient, the original catheter may be exchanged for a second catheter by simply aligning the operative segment on the guide wire with the tool to create the coupling force field; withdrawing the original catheter proximally past the tool and over the guide wire (which is held stationary relative to the tool) until the catheter is free of the guide wire; aligning the second catheter over the guide wire; and advancing the second catheter past the tool and over the guide wire until the second catheter is properly positioned. A handle, which couples fixedly to the tool and slidably to the catheter assembly, provides for ease of operation. The catheter assembly is stabilized within the tool through the use of a geometrically configured catheter receiving notch.

In yet another embodiment, the present invention includes a guide catheter exchange device and method of exchanging a guide catheter. The guide catheter exchange device includes a magnetically responsive segment located on a proximal end for maintaining a previously placed guide wire in position across the stenosis, while performing a guide catheter exchange procedure. The magnetically responsive segment can include an active magnetic segment. The guide catheter exchange device allows a guide catheter exchange procedure to be performed by a solo physician.

In one preferred embodiment, the guide catheter exchange device includes a support member having a proximal end and a distal end, and a mechanism for coupling responsive to a magnetic source, carried by the support member. The mechanism for coupling includes a magnetically active segment located on the proximal end of the support member. The device may also include a magnetically active tool which, when positioned adjacent the magnetically active segment, couples the magnetically active segment to the magnetically active tool.

The support member may include a shaft having at least one lumen extending longitudinally therethrough. The magnetically operative segment may be carried by the proximal portion of the shaft. In one embodiment, the magnetically operative segment includes a magnetically responsive member which encircles the shaft lumen. Alternatively, the magnetically responsive member may be located adjacent the shaft lumen.

In an alternative embodiment, the present invention further includes a body having at least one lumen extending longitudinally therethrough, fixedly secured to the distal end of the support member. The magnetically responsive segment, which may be carried on the proximal end of the support member, may include at least one notch.

In yet another embodiment, the present invention includes a device for controlling the movement of a guide wire relative to a guide catheter. The device includes a shaft having a proximal portion and a distal portion, and a magnetically operative segment carried by the proximal portion of the shaft.

The present invention includes a method of maintaining a guide wire stationary relative to a guide catheter located within a patient's vascular system. The method comprises the steps of inserting an exchange device having a magnetically active segment at its proximal end with respect to the guide wire, and positioning the exchange device active segment within a magnetically active captivation tool. The method also includes the step of moving the guide catheter relative to the exchange device.

Yet another method in accordance with the present invention for exchanging a guide catheter comprises the steps of inserting an exchange device having a magnetically active segment at its proximal end over a guide wire positioned within a guide catheter in a patient's vascular system. Removing the guide catheter over the exchange device. Next, inserting a second guide catheter over the exchange device. Finally, removing the exchange device. The method may also include the step of positioning the exchange device active segment within a magnetically active captivation tool.

The present invention allows a physician to perform a guide catheter exchange procedure, while maintaining a previously placed guide wire in position across a stenosis. The guide catheter exchange device allows the guide catheter exchange procedure to be performed by a solo physician.

BRIEF DESCRIPTION OF THE DRAWINGS

The invention will be further described with reference to the accompanying drawings where like numbers refer to like parts in several views and wherein:

FIG. 4 is a detail sectional view of an operative segment of a guide wire which is one preferred embodiment of the present invention.

FIG. 5 is a view in end elevation showing one preferred embodiment of the present invention.

FIG. 6 is a view in side elevation along line 6—6 in FIG. 5.

FIG. 7 is an enlarged fragmentary detail of portion A in FIG. 5 illustrating the placement of a catheter assembly, shown in section, into the tool housing.

FIG. 8 shows the catheter and guide wire pre-inserted in a vessel of a patient, with the operative segment on the guide wire disposed within the proximal end of the dilatation catheter.

FIG. 9 shows the tool being placed over the operative segment of the guide wire.

FIG. 10 shows the dilatation catheter being withdrawn over the guide wire and past the tool.

FIG. 11 shows the dilatation catheter external from the patient's body with the tool adjacent the operative segment on the guide wire.

FIG. 12 shows the dilatation catheter external to the patient's body with the tool removed from adjacent the guide wire.

FIG. 13 shows the guide wire remaining in place in the vessel of the patient with the tool and dilatation catheter removed.

FIG. 14 is a detail sectional view of an operative segment of a guide wire which is another preferred embodiment of the present invention.

FIG. 15 is a detail sectional view of an operative segment of a guide wire which is another preferred embodiment of the present invention.

FIG. 16 is a schematic illustration of a guide wire extension containing an operative segment.

FIG. 17 is a schematic illustration of a tool which includes an electromagnet.

FIG. 18 is an exploded view of the three major components of the tool of an alternative embodiment.

FIG. 22 is a perspective view of the guide catheter exchange device of the present invention.

FIG. 22A is a partial sectional view of one embodiment of the guide catheter exchange device of FIG. 22.

FIG. 22B is a partial sectional view showing an alternative embodiment of the guide catheter exchange device of FIG. 22.

FIG. 23 is a perspective view of an alternative embodiment of the guide catheter exchange device of the present invention.

FIG. 23A is a partial perspective view of the guide catheter exchange device shown in FIG. 23.

FIG. 23B is a partial cross-sectional view of one embodiment of the operative segment shown in FIG. 23.

FIG. 23C is a partial sectional view of one embodiment of the operative segment shown in FIG. 23.

FIG. 23D is a cross-sectional view of the operative segment shown in FIG. 23C.

FIG. 23G is a perspective view of an alternative embodiment of the guide catheter exchange device of the present invention.

FIG. 24 is an alternative embodiment of the guide catheter exchange device of the present invention.

FIG. 24A is a partial sectional view of the operative segment of the guide catheter exchange device shown in FIG. 24.

While the above identified drawing features set forth preferred embodiments, other embodiments of the present invention are also contemplated, as noted in the discussion. This disclosure presents illustrative embodiments of the present invention by way of representation and not limitation. It should be understood that numerous other modifications and embodiments can be devised by those skilled in the art which fall within the scope and spirit of the principles of this invention. It should be noted that the figures have not been drawn to scale as it has been necessary to enlarge certain portions for clarity.

DETAILED DESCRIPTION OF THE PREFERRED EMBODIMENTS

The present invention is a method and device for controlling movement of an elongated shaft in the catheterization of a patient, where a portion of the shaft is inserted within the patient. More precisely, the present invention is a method and device for controlling the movement of an elongated shaft extending through an elongated tube, wherein a portion of both the tube and shaft are inserted within the patient. In one preferred embodiment, the shaft is a guide wire and the tube is a catheter with a lumen for slidably receiving the guide wire.

Figure 1:
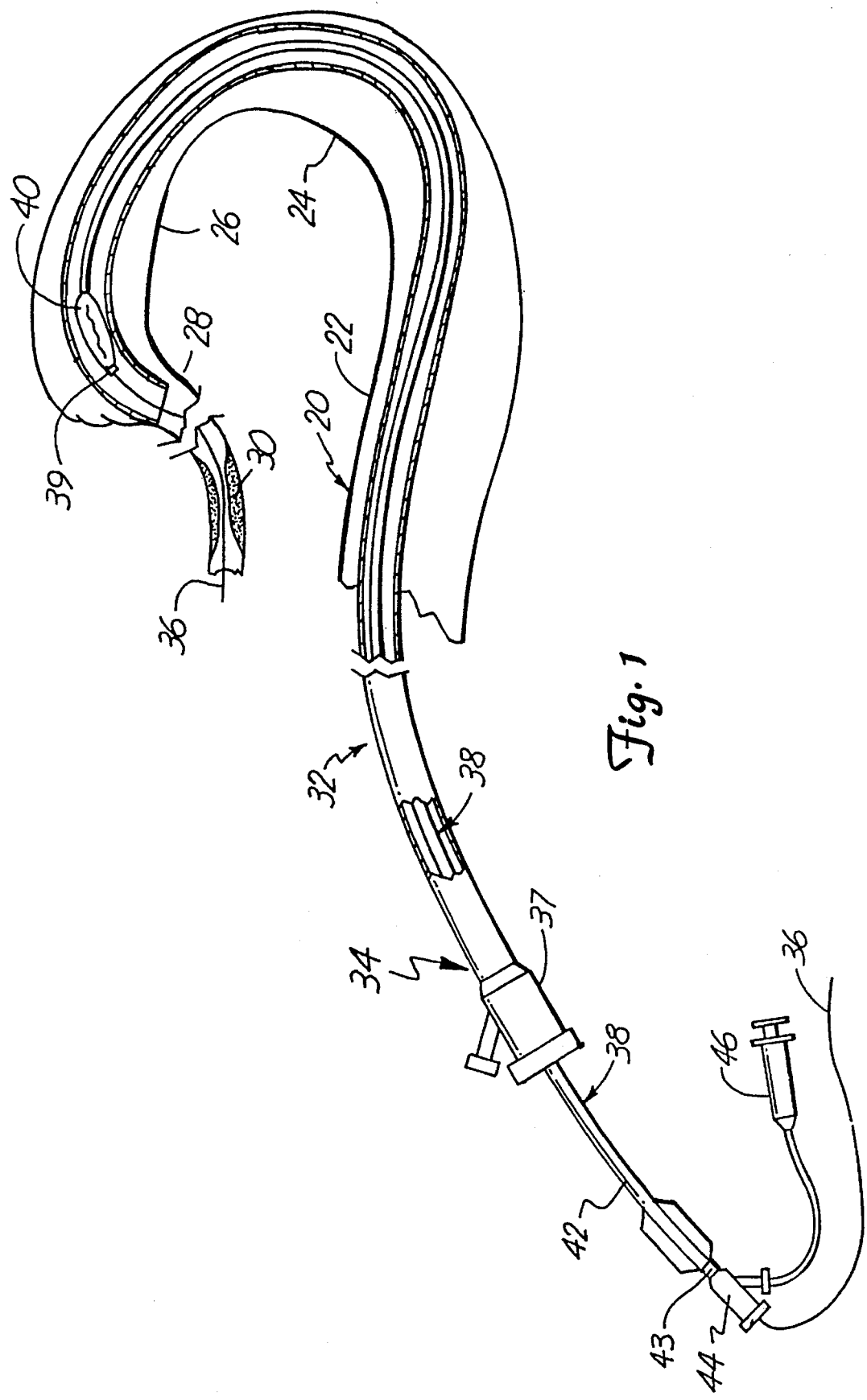
FIG. 1 is a diagrammatic view of an angioplasty catheter system in the vascular system of a patient.

A vascular system 20 and an angioplasty catheter system 32 are shown in FIG. 1. In an angioplasty procedure, entry into the vascular system 20 is typically through the femoral artery in the thigh (as schematically shown at 21 in FIGS. 2 and 8). A distal portion of the vascular system 20 includes a descending aorta 22, an aortic arch 24, and an ascending aorta 26. Extending from the ascending aorta 26 is a coronary artery 28, in which a stenosis 30 is formed.

The angioplasty catheter system 32 includes a guide catheter 34, a guide wire 36 extending through the guide catheter 34, and a dilatation catheter 38 with an inflatable balloon 40 mounted at a distal end 39 of a main tubular shaft 42 of the dilatation catheter 38. The dilatation catheter 38 is designed for use in conjunction with a guide wire, and has a guide wire lumen 45 (FIGS. 2, 3 and 7) extending along its entire length. The dilatation catheter 38 also has an inflation lumen 47 extending therethrough. The dilatation catheter 38 may be a dual lumen or coaxial lumen structure. In a coaxial arrangement (as shown), the inflation lumen 47 is provided between the outer main shaft 42 and an inner tubular shaft 41 disposed coaxially within the outer shaft 42. The guide wire lumen 45 is thus defined by the interior of the inner tubular shaft 41.

As illustrated in FIG. 1, a proximal portion of the guide wire 36 protrudes proximally out of a proximal end 43 of the dilatation catheter 38 and a proximal portion of the dilatation catheter 38 protrudes proximally out of a Y-adaptor 37 connected to a proximal end of the guide catheter 34. An inflation manifold 44 is connected to the proximal end 43 of the dilatation catheter 38 for facilitating inflation of the balloon 40. An inflation device 46 for inflating the balloon 40 is in fluid communication with the balloon 40 via the inflation manifold 44 and the inflation lumen 47.

The basic angioplasty procedure consists of inserting the guide catheter 34 into the vascular system 20 at the femoral artery. The guide catheter 34 is advanced through the vascular system 20 until a distal end of the guide catheter 34 is adjacent the mouth of the coronary artery 28 as shown in FIG. 1. Next, the distal end 39 of the dilatation catheter 38 is loaded onto and over a proximal end of the guide wire 36 and advanced over the guide wire 36 until the distal end 39 of the dilatation catheter 38 is adjacent a distal end of the guide wire 36. Then, the assembled combination of the guide wire 36 and the dilatation catheter 38 is inserted into the proximal end of the guide catheter 34 and advanced distally therethrough, retracing the already established path of the guide catheter 34 through the patient's vascular system 20. The guide wire 36 and the dilatation catheter 38 combination typically is advanced distally until adjacent the distal end of the guide catheter 34. The distal tip of the guide wire 36 is then advanced separately and manipulated into the artery tree to and across the stenosed artery. The dilatation catheter 38 is then advanced over the guide wire 36 to position the balloon 40 across the stenosis 30. The balloon 40 is inflated to dilate the stenosis 30 to re-establish acceptable blood flow through the artery.

However, sometimes the dilatation catheter 38 must be exchanged for another dilatation catheter to complete the angioplasty procedure. When exchanging the dilatation catheter 38 for another catheter, it is desirable to hold the guide wire 36 in place across the stenosis 30 during withdrawal of the dilatation catheter 38 (and advancement of the next catheter) to eliminate the need to re-establish the position of the guide wire 36 by retracing the tortuous path to the stenosis 30 after the dilatation catheter 38 is exchanged. Maintaining the guide wire 36 in place after an initial dilatation also provides the physician with a path through the stenosis 30 in case of an abrupt closure of the vessel.

Figure 2:
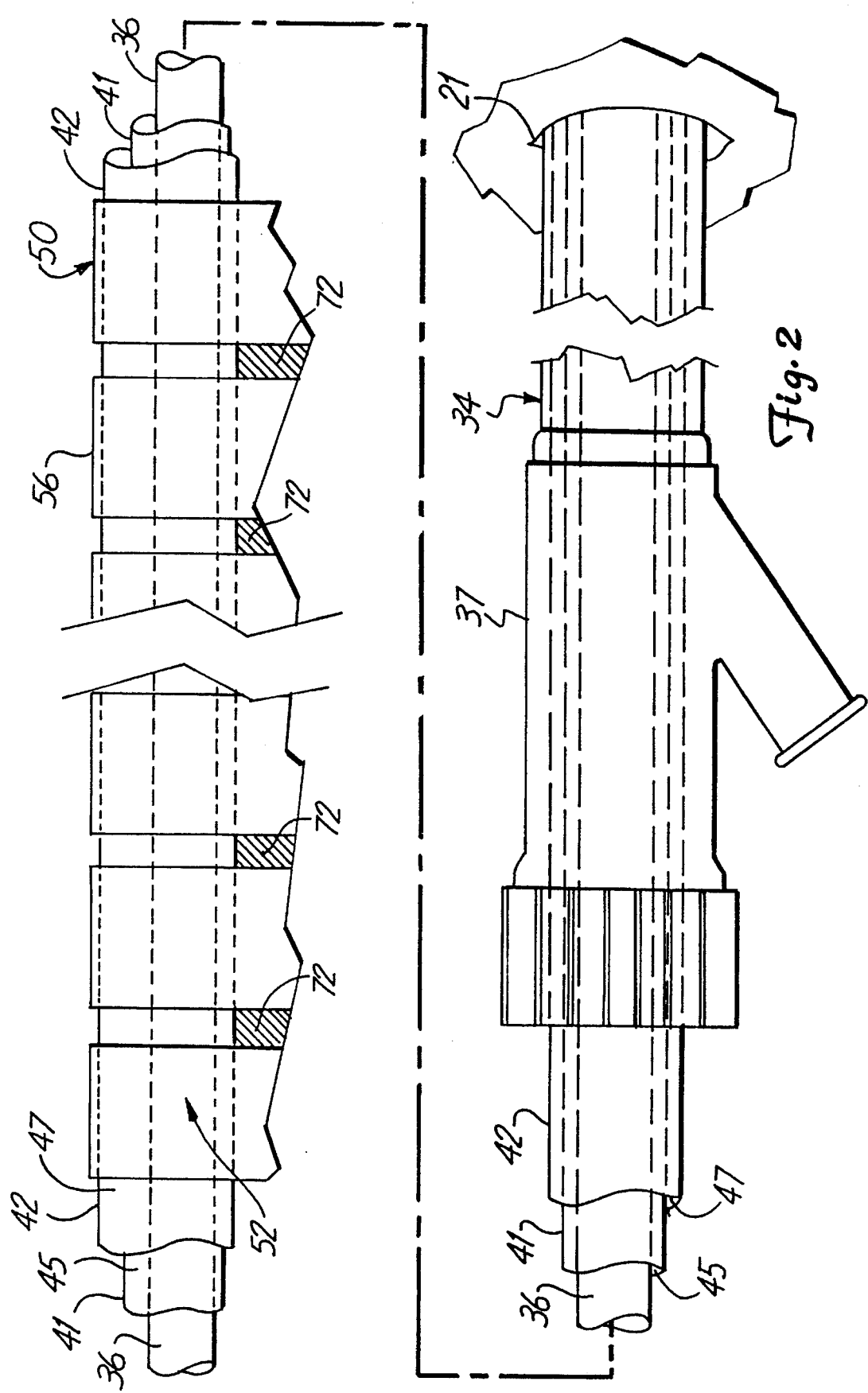
FIG. 2 is an enlarged view in side elevation of one embodiment of the present invention which shows guide wire captivation.

The present invention facilitates holding the guide wire 36 in place across the stenosis 30 without requiring an exchange wire, an extension wire or additional intravascular devices to accomplish the dilatation catheter exchange over the guide wire 36. In one form of the present invention, means are provided proximally of the guide catheter Y-adaptor 37 to cooperate with the guide wire 36 for maintaining the position of the guide wire 36 across the stenosis 30. One preferred embodiment of the present invention, as shown in FIGS. 2–7, employs a captivation tool 50 which cooperates with an operative segment 52 of the guide wire 36 to create a coupling force field between the tool 50 and the operative segment 52. The coupling force field is defined by an energy field (such as a magnetic field). The force generated by the field is strong enough to maintain the position of the guide wire 36 relative to the tool 50 when the dilatation catheter 38 is aligned over the operative segment 52 of the guide wire 36, and particularly when the dilatation catheter 38 is moved over the guide wire 36. As shown in FIG. 2, the operative segment 52 of the guide wire 36 is located on a proximal portion of the guide wire 36 and is positioned so that the operative segment 52 is located some distance beyond the proximal end of the guide catheter Y-adaptor 37.

Figure 3:
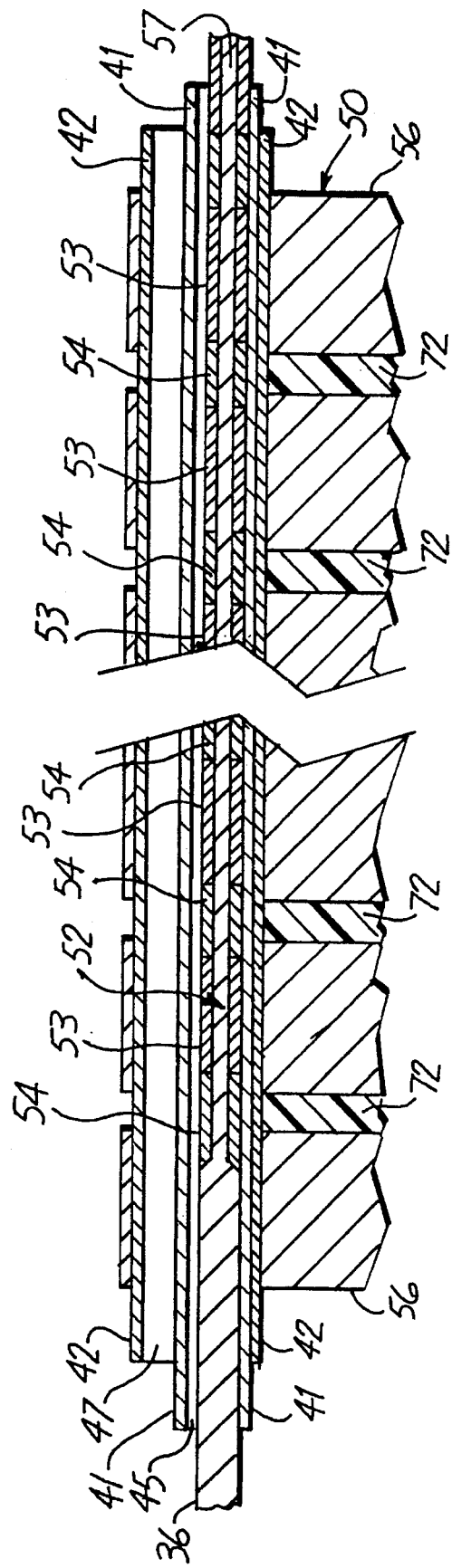
FIG. 3 is a sectional view of the captivation tool in FIG. 2.

As seen in FIG. 3, the operative segment 52 of the guide wire 36 includes a plurality of magnetically permeable segments 54 secured on the guide wire 36 at locations along the guide wire 36. (Examples of suitable magnetically permeable materials are Rodar, manufactured by T. N. Wilbur B. Driver Company and available in tube form from Uniform Tubes of Collegeville, Pa.; Hiperco Alloy 50, manufactured by Carpenter Steel of Reading, Pa.; Permendur or 2V Permendur, listed as high permeable magnetic materials having large saturation flux densities in the CRC Handbook of Chemistry and Physics, 47th ed.; or any other material with a suitably large residual induction). In this embodiment, as seen in FIGS. 3 and 4, the operative segment 52 includes a plurality of magnetically permeable segments 54 secured about a reduced diameter portion 57 of guide wire 36. Non-magnetically permeable segments 53 are disposed between and about each of the magnetically permeable segments 54, respectively. In all embodiments of the operative segment 52 on the guide wire 36, the outside diameter of the operative segment 52 stays essentially the same as the outside diameter of the guide wire 36, and the transitions between magnetically permeable and non-magnetically permeable materials are smooth.

As seen in FIGS. 5–7, the captivation tool 50 includes a housing member 56. The housing member 56 includes a longitudinal slot 60 defined by a pair of side slot surfaces 62 and 64, and a bottom slot surface 66. The slot 60 provides a space with sufficient size to slidably receive the dilatation catheter 38 and allow the dilatation catheter 38 to longitudinally pass freely through the slot 60, yet still restrict lateral movement of the dilatation catheter 38 between the slot surfaces 62, 64, and 66.

The housing member 56 also includes a plurality of rectangular-shaped magnetic sections 72 (shown in phantom in FIG. 5) which have exposed surfaces at bottom slot surface 66. As best seen in FIG. 6, the magnetic sections 72 are provided at longitudinally spaced locations along the housing member 56 corresponding to the spacing of the magnetically permeable sections 54 on the guide wire 36. The magnetically permeable sections 54 on the guide wire 36 and the magnetic sections 72 in the housing member 56 are spaced such that they can be aligned across from each other as shown in FIG. 3. Although the material of the bottom slot surface 66 alternates between the housing member 56 and the magnetic sections 72, the bottom slot surface 66 is smooth. The magnetic sections 72 are preferably made from a strong magnetic material with a large cohesive force (such as neodynium boron iron) that can hold a magnetization through a relatively thin section.

The size and spacing of the magnetic sections 72, as well as the size and spacing of the magnetically permeable sections 54 of the operative segment 52 on the guide wire 36, are chosen to maximize the longitudinal attractive force on the guide wire 36 while minimizing the radial attractive force on the guide wire 36. The net force for maintaining the position of the guide wire 36 relative to the tool 50 is governed by the equation:

$$F_{net} = F_L - \mu F_R$$

where $F_{net}$ is the net force available to maintain the position of the guide wire 36, $F_L$ is the longitudinal force of attraction between the tool 50 and the operative segment 52 on the guide wire 36, $F_R$ is the radial force of attraction between the tool 50 and the operative segment 52, and $\mu$ is the friction coefficient between the guide wire 36 and the dilatation catheter 38.

Thus, to obtain optimum performance from the device, it is desireable to maximize the force $F_L$ and minimize the force $F_R$ and the friction coefficient $\mu$. The friction coefficient $\mu$ may be reduced through the use of lubricous coatings and materials, and the attractive forces $F_L$ and $F_R$ may be optimized through the use of mathematical modeling techniques known in the art. For example, positioning the magnetic sections 72 in the tool 50 such that the polarity of the magnetic sections 72 alternates between magnetic-sections 72 reduces the radial attractive force $F_R$. Such alternation increases the total effective magnetic field, thereby increasing the longitudinal holding force. The total coupling force between the operative segment 52 and the tool 50 is proportional to the number of magnetic sections 72 in the tool 50.

In one preferred embodiment, the guide wire 36 has an outside diameter of 0.018 inches. The operative segment 52 has a length of approximately 10 inches with approximately 50 magnetically permeable sections 54, each having a length of 0.1 inch, separated by non-magnetically permeable sections 53 with a length of 0.1 inch. A non-operative segment approximately 2 inches long is attached to the proximal end of the operative segment 52. The tool 50 is approximately 4.0 inches long, 1.0 inch high, and 1.0 inch wide, with 20 magnetic sections (magnets) 72 spaced 0.2 inches apart. The magnetic sections 72 are 0.04 inches thick and 0.75 inches high, with a width of 0.75 inches. The height and width of the magnetic sections 72 are determined as a function of the thickness of the magnetic sections 72. The magnetic poles of the magnetic sections 72 are alternated so that like poles of the spaced magnetic alternated so that like poles of the spaced magnetic sections 72 are facing each other. The slot 60 for receiving the dilatation catheter 38 is 0.10 inch wide and 0.10 inch deep. The holes 68 centered under each of the magnetic sections 72 (for gluing magnetic sections 72 in place during assembly) are approximately 0.04 inches in diameter.

Figure 9:
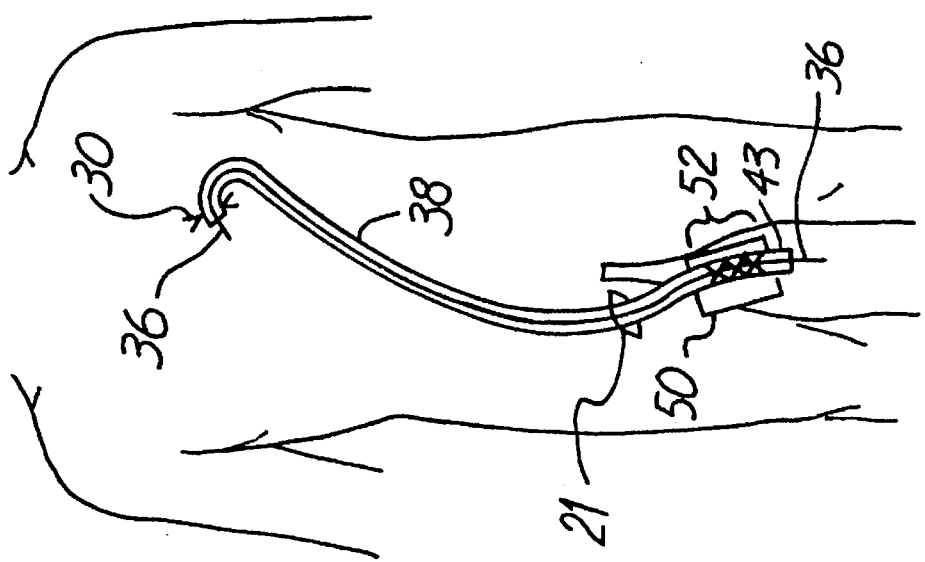
FIGS. 8–13 depict a preferred method of use for the present invention.
Figure 8:
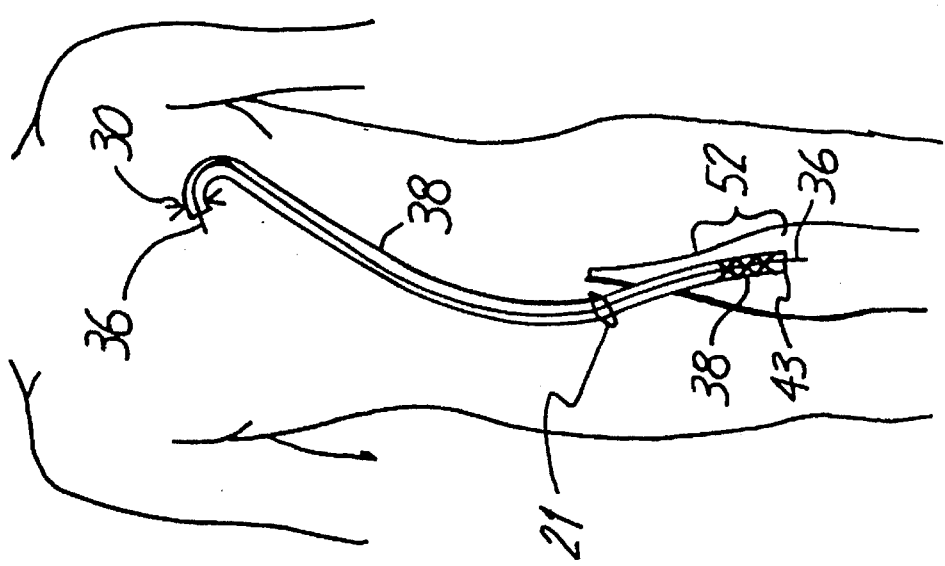

The device of the present invention for facilitating a dilatation catheter exchange while maintaining a guide wire in place within a vessel is employed in the following manner. Of course, performing such an exchange requires that the angioplasty catheter system 32 already be in place in the vascular system 20 of the patient as previously described. As such, the proximal end of the guide wire 36 and the proximal end 43 of the dilatation catheter 38 protrude proximally outside the patient as seen in FIG. 8, with the proximal end of the guide wire 36 extending proximally beyond the proximal end 43 of the dilatation catheter 38. Recall that the operative segment 52 of the guide wire 36 (identified schematically by the "xxx's" in FIGS. 8–13) is located near the proximal portion of the guide wire 36 and is disposed within the proximal end 43 of dilatation catheter 38. To begin the exchange, the physician grasps the proximal end of the guide wire 36 to maintain its distal end in place across the stenosis 30. The physician then places a proximal portion of the dilatation catheter 38 (having the operative segment 52 extending therein) into the slot 60 of the housing member 56 (see FIGS. 7 and 9) and aligns the operative segment 52 with the tool 50.

The alignment of the operative segment 52 with the tool 50 is relatively simple because the operative segment 52 is longer than the slot 60 in the tool 50, and the distance between the magnetically permeable sections 54 on the guide wire 36 and the corresponding magnetic sections 72 on the tool 50 is relatively small. The result is that when the operative segment 52 is positioned within the slot 60 of the tool 50 only a small amount of movement (less than half the distance between the magnetic sections 72 on the tool 50) is required to align the magnetically active portions of the operative segment 52 and the tool 50. As the spacing between the magnetic sections 72 becomes smaller, less movement is required to align the tool 50 and the operative segment 50. At the given dimensions, the tool 50 and the operative segment 52 effectively become self-aligning, and simply positioning the operative segment 52 within the slot 60 of the tool 50 ensures proper alignment.

Once the operative segment 52 on the guide wire 36 is properly aligned with the magnetic sections 72 of the captivation tool 50, the guide wire 36 is attracted to the captivation tool 50 by the resultant magnetic field created therebetween (see FIGS. 2, 3, and 7). This results in the guide wire 36 being pulled (along with the dilatation catheter shafts 41 and 42) against the bottom slot surface 66 of the housing member 56 as seen in FIGS. 3 and 7. The drawings are exaggerated for clarity in this regard.

Once the guide wire and tool 50 have been so coupled, the physician releases the guide wire 36 proximal to the tool 50 and then grasps the proximal end 43 of the dilatation catheter 38 proximally of the tool 50. The dilatation catheter 38 is pulled proximally over the guide wire 36 and past the tool 50 while holding the tool 50 (and thus the guide wire 36) in a stationary position relative to the patient (see FIG. 10). The physician may choose to hold the tool 50 in his hand, or alternately the physician may place the tool 50 on the table to hold the tool 50 stationary. The longitudinal magnetic attraction between the guide wire 36 and the captivation tool 50 is greater than the friction between the guide wire 36 and the inner catheter shaft 41. Accordingly, the dilatation catheter 38 may be pulled over the guide wire 36 while maintaining the guide wire 36 in the same position relative to the captivation tool 50. This ultimately maintains the guide wire 36 in position across the stenosis 30 during this maneuver, as long as the tool 50 is held generally stationary with respect to the patient.

Figure 11:
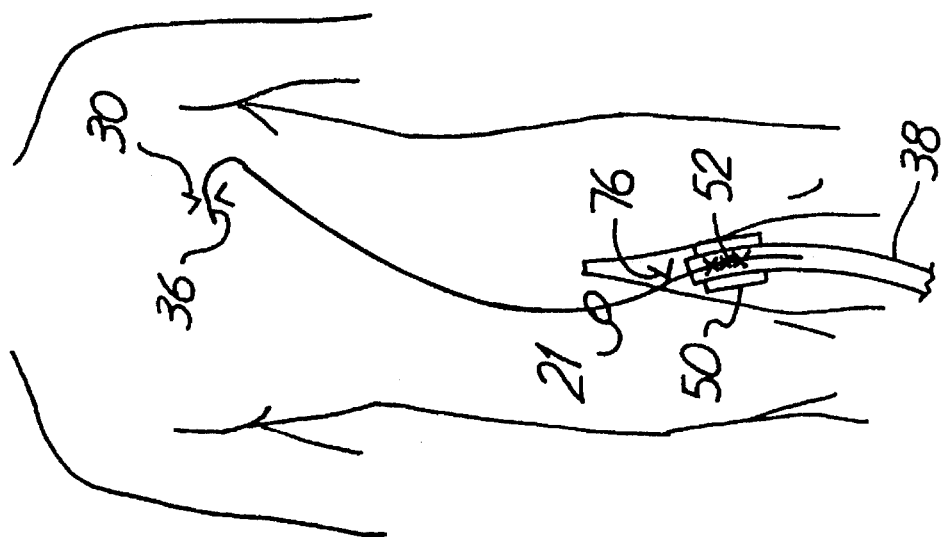
Figure 10:
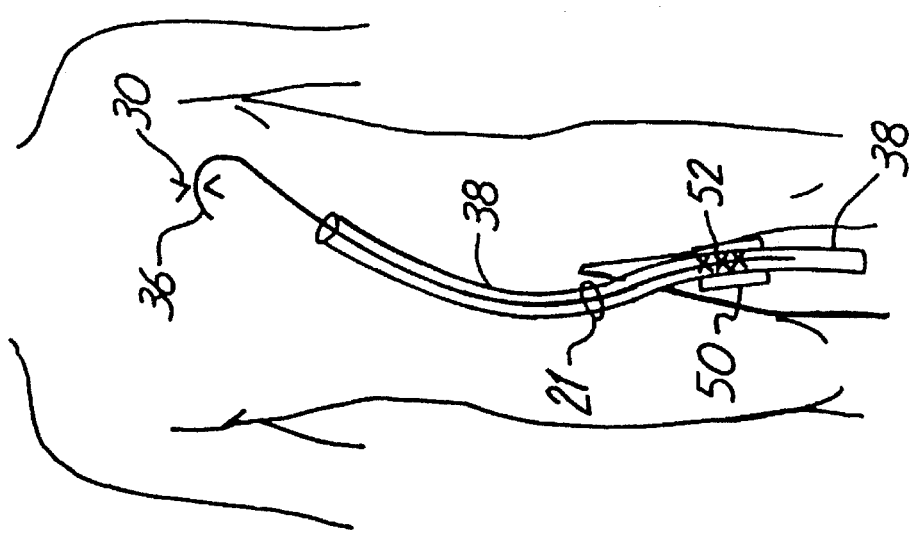
Figure 13:
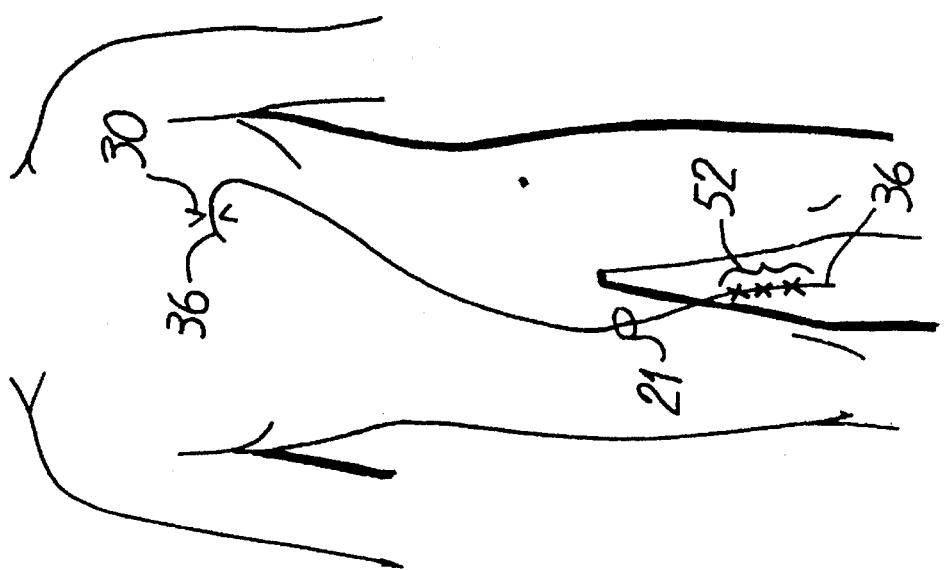

The catheter 38 is withdrawn until the distal end of the dilatation catheter 38 is exposed outside of the patient's body as seen in FIG. 11. As such, a portion of the guide wire 36 will be exposed between the distal end of the catheter 38 and the proximal end of the guide catheter 34, which protrudes outside the patient's body. The physician then grasps this exposed portion of the guide wire 36 distal to the tool 50 and the distal end of the dilatation catheter 38 as at 76. The physician then laterally separates the catheter 38 and the guide wire 36 therein from the tool 50 by overcoming the radial magnetic forces between the guide wire operative segment 52 and the tool 50. The physician then completely withdraws the first balloon catheter 38 proximally off of the guide wire 36. The guide wire 36 has thus been held in a generally stationary position during the entire catheter removal procedure in a very simple and elegant manner, which can be managed by the physician without the need for extra persons to hold or manipulate additional catheter or guide wire components.

Next, while still maintaining the guide wire 36 in place by grasping at 76, a second dilatation catheter is placed on the proximal end of the guide wire 36 and moved distally over the guide wire 36 until the operative segment 52 of the guide wire 36 is positioned within a distal end of the second dilatation catheter (preferably within the second catheter at a point proximal to the balloon thereon). The operative segment 52 of the guide wire 36 and the tool 50 are positioned together (as previously described) until the operative segment 52 is magnetically aligned with the magnetic sections 72 of the captivation tool 50. The physician then releases the guide wire 36 distally of the tool 50 as at 76, grasps the second dilatation catheter, and distally advances the second dilatation catheter over the guide wire 36 longitudinally relative to tool 50 and the guide wire 36 to distally advance the second catheter through the guide catheter 34. During dilatation catheter advancement, the captivation tool 50 is held stationary relative to the patient to ultimately maintain the distal end of the guide wire 36 in place across the stenosis 30. The second dilatation catheter is advanced distally over the guide wire 36 until the proximal end of the guide wire 36 extends beyond a proximal end of the second dilatation catheter. The physician then grasps the guide wire 36 proximal to the tool 50 and dilatation catheter manifold 44, and separates the second dilatation catheter and the guide wire 36 therein from the tool 50. The second dilatation catheter is then further advanced distally over the guide wire 36 until the balloon of the second dilatation catheter is across the stenosis 30 for dilatation. The dilatation catheter exchange procedure using the captivation tool 50 and operative segment 52 can thus be repeated in this manner as necessary.

During the dilatation catheter removal and insertion procedure, the position of the guide wire 36 is maintained relative to the guide catheter 34, and more importantly, relative to the stenosis 30. The present invention is ideally suited for facilitating catheter exchanges without the need for a long exchange guide wire, a modified catheter, or additional intravascular devices such as a guide wire holding balloon for "trapping" the guide wire against a wall of the guide catheter. The present invention allows catheter exchanges over a standard length guide wire using a catheter having a full length guide wire lumen. Additionally, the procedure may be performed by a single physician and without the prolonged use of X-ray fluoroscopy used to observe the position of the guide wire, since the guide wire is held stationary by use of the present invention and thus its position need not be continuously observed.

Figure 12:
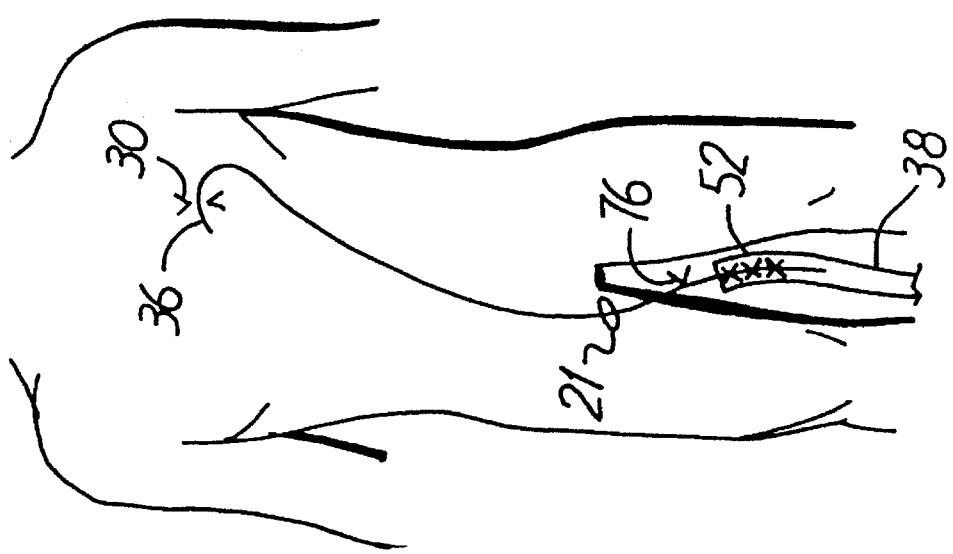

The utility of the present invention is not limited to catheter exchange procedures. The present invention may be used as a "third hand" during a catheterization procedure. Typically during a catheterization procedure, the physician is required to simultaneously manipulate the guide wire 36, the dilatation catheter 38, and the guide catheter 34. The simultaneous manipulation often requires the use of additional medical personnel, which increases the cost and complexity of the procedure. By placing the operative segment 52 adjacent the tool 50 and securing the tool 50 itself in a stationary position, the present invention eliminates the need for the physician (or a second person) to continually hold the guide wire 36 during the procedure. The operative segment 52 provided on the guide wire 36 can be made long enough to allow the use of more than one tool 50 during a catheterization procedure. For example, when the physician is withdrawing the dilatation catheter 38 from the patient and is required to grasp the guide wire 36 before completely removing the dilatation catheter 38 from the guide wire 36 (e.g., when the physician grasps the guide wire 36 at 76 before completely withdrawing the dilatation catheter 38 of the guide wire 36, as seen in FIGS. 11 and 12 and as previously described), a second tool 50 may be used in place of the physician actually grasping the guide wire 36.

Figure 21:
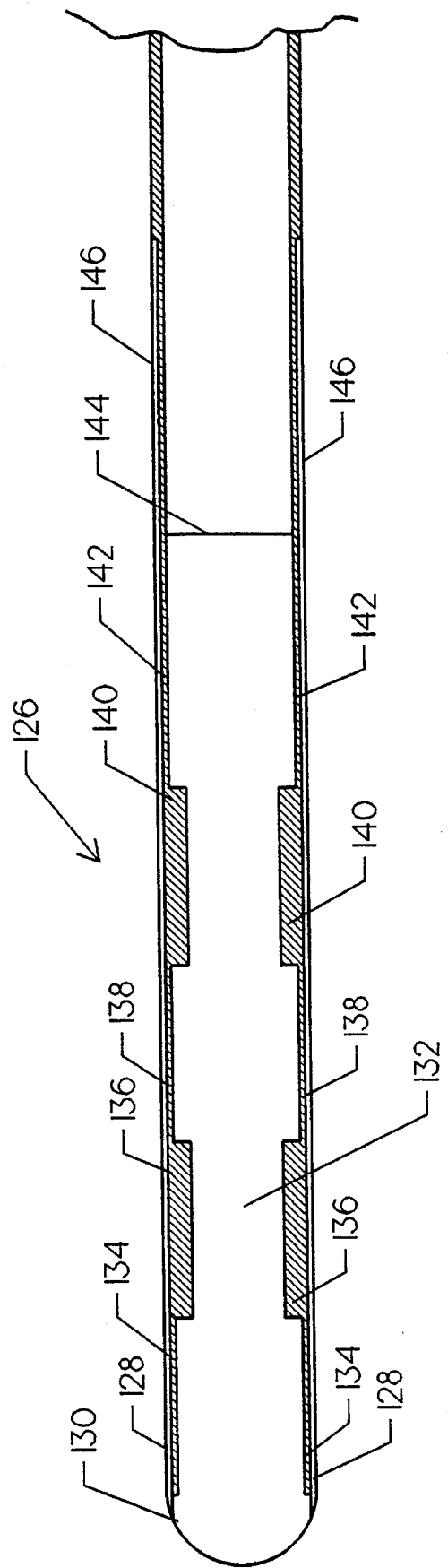
FIG. 21 is a longitudinally sectioned view of the proximal end of the guide wire of the preferred embodiment.

In alternate embodiments, the operative segment 52 on the guide wire 36 may take a number of forms including those shown in FIGS. 14, 15 and 21. In FIG. 14, each of a plurality of non-magnetically permeable segments 58 are secured about reduced diameter portions 55 of the guide wire 36A. The guide wire 36A is made of a magnetically permeable material, and segments 58 are a non-magnetically permeable material such as plastics or non-magnetic metals. As seen in FIG. 15, the operative segment 52 may include an elongate non-magnetically permeable tubular member 51 with a plurality of solid cylindrically-shaped magnetically permeable segments 54A secured within member 51. The tubular member 51 is connected to a reduced diameter portion 59 of the guide wire 36. Another embodiment of the operative segment 52 is a guide wire segment made of a single material which can exist in either a magnetic or non-magnetic state (such as martensite of austenite steel) depending upon the heat treatment of the material. Alternating sections of the wire are heat treated locally to form alternating magnetic and non-magnetic sections on the guide wire. In each embodiment of the operative segment 52, the magnetically permeable material may be replaced with permanent magnets.

The operative segment 52 may be provided on a short guide wire extension 74 (e.g., about 12 inches long) for a standard guide wire. As shown schematically in FIG. 16, this short extension 74 would connect to the proximal end of the standard guide wire 76 in a conventional manner, such as shown, e.g., in U.S. Pat. Nos. Gambale et al. 4,922,923; Messner et al. 4,875,489; Crittenden et al. 5,035,686; or Palmer et al. 5,117,838. The short extension 74 is selectively attachable to the standard guide wire 76 and can be connected and disconnected multiple times during a single procedure. Use of the short guide wire extension 74 with an operative segment 52 allows the physician to perform a catheter exchange using the present invention even if the catheterization procedure was started using a standard guide wire 76. The use of the short extension 74 in a catheter exchange merely requires the additional acts of attaching the extension 74 to the guide wire 76 and withdrawing the original catheter proximally far enough to cover the operative segment 52 on the short extension 74 before positioning the dilatation catheter 38 relative to the tool 50 for magnetic coupling of the extended guide wire and the tool 50. Otherwise, the use of such a short guide wire extension 74, either for holding the wire/catheter assembly during the procedure or to facilitate a catheter exchange over a stationary wire, is essentially the same as described herein.

The tool 50 may be adapted to fit over the guide catheter 34 (as in a 2-piece "clam shell" design), may be made in the form of a guide catheter extension, or may be incorporated directly into the guide catheter Y-adaptor 37, for example. Additionally, the tool 50 may be designed such that the magnetic sections 72 in the tool 50 are moved within the housing member 57 and away from the slot 60 in the housing member 56. With this feature, the attraction between the tool 50 and the operative segment 52 on the guide wire 36 is effectively "turned off" when the magnetic sections 72 are moved sufficiently laterally away from the slot 60 in the housing member 56 and the operative segment 52 of the guide wire 36 therein to break the magnetic attraction therebetween.

The three major components of an alternative embodiment of the tool are shown in exploded view 100 in FIG. 18. Magnet fixture block 108 receives permanent magnets (not shown) in magnet receiving slots 104 as described above. Preferably, the magnets are placed with alternating polarity to increase the effective axial holding force and decrease the effective normal force which reduces longitudinal friction. Magnet fixture block 108 is preferably molded of a polycarbonate, with General Electric Lexan HP2X-42046 being the recommended material.

Bottom block 102 is molded of a similar but clear material, such as General Electric Lexan HP2X-111, and engages with magnet fixture block 108, through receiving channel 101. In operation, magnet fixture block 108 is held within receiving channel 101 by the engagement of longitudinal protrusions 116 and 114 of magnetic fixture block 108 within longitudinal channels 115 and 117 of bottom block 102, respectively. Configured catheter receiving notch 118 stabilizes the position of the catheter assembly as discussed in greater detail below.

Operator handle 111 is molded of Lexan HP2X-111 (clear) material. It has a catheter receiving element 112 and a configured engagement latch 110, which is fixedly engaged within receiving notch 103 of bottom block 102 and receiving notch 105 of magnet fixture block 108.

Figure 19:
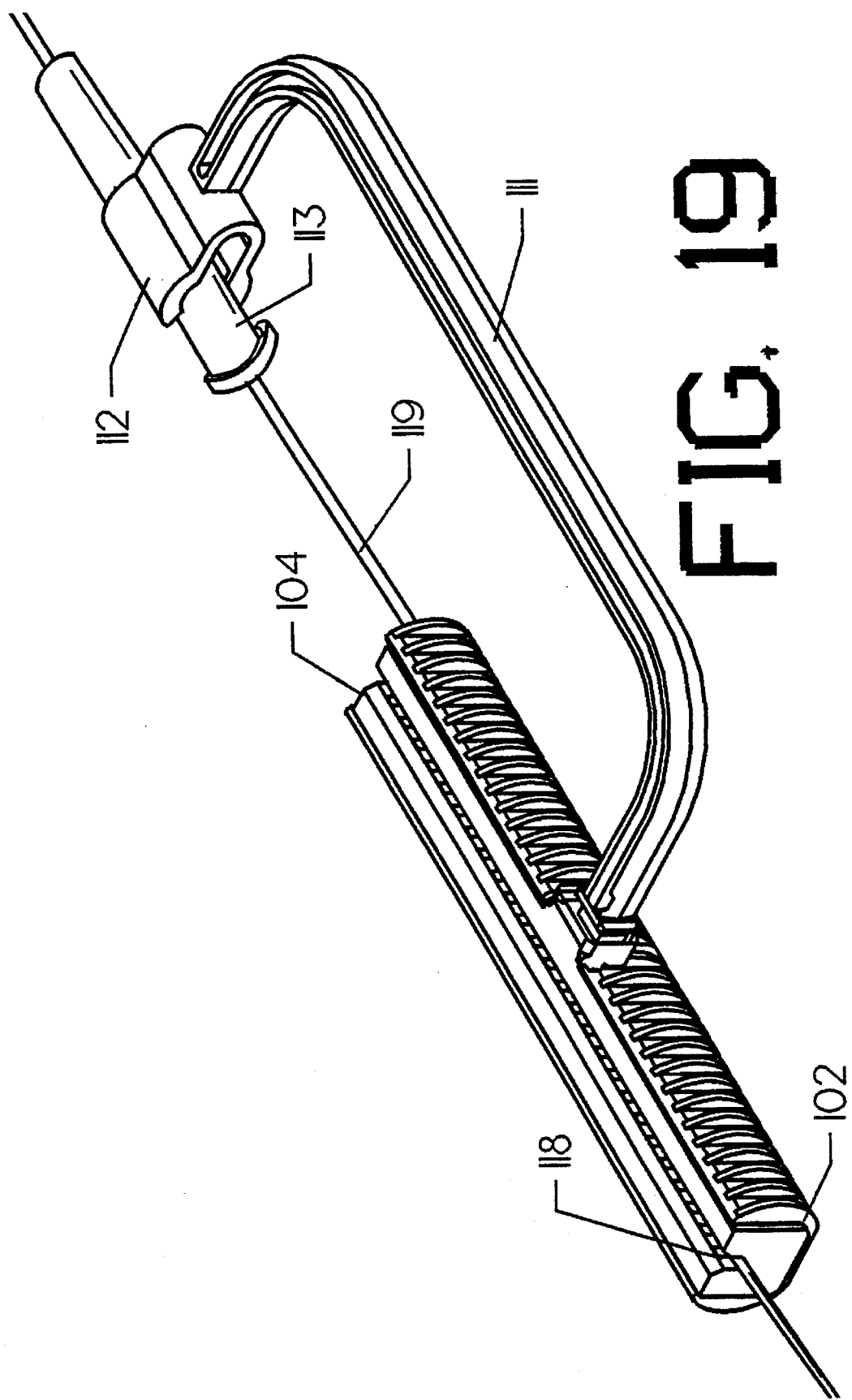
FIG. 19 is an isometric view of the operation of the alternative embodiment of FIG. 18.

FIG. 19 is a isometric composite view of the alternative embodiment of FIG. 18 in operation. Catheter receiving element 112 slidably engages y-adapter 113 of catheter assembly 119 as shown. Catheter assembly 119 is stabilized within configured catheter receiving notch 118. The operator conveniently grasps the entire assembly using handle 111.

Figure 20:
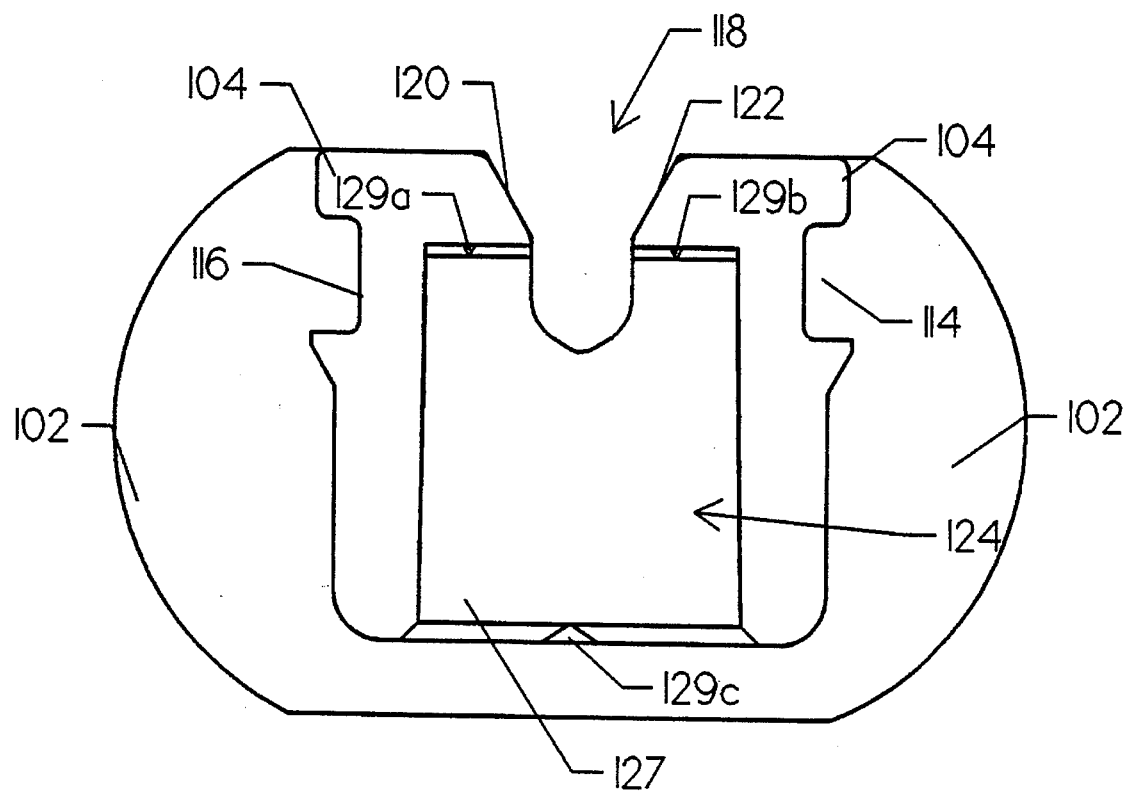
FIG. 20 is a close up view of the catheter receiving notch of the alternative embodiment.

A cross sectional view of the assembled tool is shown in FIG. 20. Inclines 120 and 122 direct catheter assembly 119 into catheter stabilization channel 118, which is configured to hold catheter assembly 119 within the above described magnetic field. Permanent magnet 127 is shown held in place by contact with molded spikes 129a, 129b, and 129c.

An alternative embodiment of the proximal end of guide wire active area 126 is shown in longitudinal sectioned view 21. The inner core 132 of the assembly is preferably a wire of Hyperco 50B, which is an alloy of 48.5% cobalt, 48.5% iron, and 3% vanadium. It is commercially available as explained above and has a diameter of about 0.011 inch.

Inner core 132 is circumferentially ground to produce a reduced diameter of about 0.0045 inch for a distance of about 0.075 inch at areas 136 and 140, which are separated by distance 138, also about 0.075 inch. Proximal distance 134 is about 10.075 inches, and distance 142 is about 0.5 inch. The proximal end of a standard spring coil guide (not shown for clarity) is butt welded to distal end 144 of inner core 132.

Inner core 132 is coated with an adhesive, which is preferably Hysol 9412 to fill the ground areas 136 and 140 to an overall depth at the unground areas of about 0.001 inch. The resulting structure has a uniform outside diameter of about 0.011 inch, which is covered before curing is completed by hypotubing 128 of 304 stainless steel. The wall thickness of hypotubing 128 is chosen to provide a standard finished outside diameter, such as 0.018 or 0.014 inch. Hypotubing 128 extends distally of distal end 144 of inner core 132 by at least 0.5 inch along area 146 to provide strain relief to the butt weld at distal end 144. Proximal end 130 is ground to a smooth hemispherical shape.

Another way to selectively apply a magnetic field between the operative segment of the guide wire and the tool is to form the magnet on the tool as an electromagnet. As illustrated diagrammatically in FIG. 17, a guide wire (or guide wire extension) 86 includes an operative segment 52 (as previously described) and the guide wire 86 is, in use, inserted within a lumen of a catheter 88. A tool 90 in this embodiment includes an electromagnet 92 which has selectively activated sections therein aligned to cooperate within the operative segment 52, and which is connected to a current source 94 through an on/off switch 96. Operation of the switch 96 thus controls the application of current to the electromagnet 92 and the creation of a magnetic field thereby. The selectively activated sections within the tool 90 may be energized by wall current (AC) or rectified wall current (DC), either of which can be turned off by switch 96 to break the holding force between the tool 90 and the guide wire 86.

It is also contemplated that alternate forms of coupling forces may be used in the present invention. For instance, instead of using permanent magnets or electromagnets, the coupling force field between the guide wire and the captivation tool may be generated by the use of electrostatic or electric fields. In each case, the coupling force between the tool and the guide wire can operate through the catheter body, and there is no contact required between the tool and the guide wire.

In yet another embodiment, the present invention includes a guide catheter exchange device and method of exchanging guide catheters. The guide catheter exchange device allows physicians to exchange guide catheters solo during catheterization procedures. The guide catheter exchange device is useful for many catheterization procedures, including diagnostic, angiography and percutaneous transluminal angioplasty procedures.

As detailed previously within this specification, a dilatation balloon system is placed within a patient's vascular system by first inserting a guide catheter through the patient's femoral, brachial, radial or any other arterial access point and advancing it through the patient's vascular system to a point near the stenotic lesion to be treated. A guide wire is advanced through the guide catheter lumen, with the distal end of the guide wire positioned across the stenosis. A dilatation catheter, having a balloon located at its distal end is advanced over the guide wire until the balloon is positioned over the stenosis for treatment of the stenosis.

Once a balloon dilatation system is in place, it may become necessary for a physician to perform a guide catheter exchange procedure to exchange the first guide catheter for a second, and sometimes larger, guide catheter. Circumstances which may require such a procedure may include the physician's need to accommodate a larger dilatation balloon catheter, the need to locate a stent in the region of the stenosis, or the need to use atherectomy (or treatment requiring larger devices), or the weakening of the present guide catheter due to an angioplasty procedure.

During a guide catheter exchange procedure, it is desirable to maintain the position of the already placed guide wire across the stenosis. As previously stated, repeated guide wire insertions increase the risk of injury to the patient and also increase the time required for the procedure. It also requires exposure of the patient to additional radiation because of the additional fluoroscopy which is required to properly place the successive guide wires across the stenosis. Maintaining the guide wire in place after an initial dilatation also provides the physician with a path through the stenosis in case of an abrupt closure of the vessel.

Due to the size of the guide catheter relative to the guide wire, additional structural support is necessary to facilitate exchange of the guide catheter while maintaining the position of the guide wire across the stenosis. It also may be desirable to provide protection for the guide wire during the guide catheter exchange procedure.

Present guide catheter exchange systems often require the use of longer guide wires or "extension" wires. The use of extension wires are cumbersome to physicians and do not allow the exchange procedure to be performed solo. One such system is disclosed in Teirstein et al. (U.S. Pat. No. 5,234,407) which is herein incorporated by reference.

The present invention allows a guide catheter exchange procedure to be performed by a solo physician without the need of exchange wires, while maintaining the position of a previously inserted guide wire across the stenotic lesion. FIG. 22 shows a guide catheter exchange device in accordance with the present invention generally at 200. The guide catheter exchange device 200 generally includes a body 202 and a support member 204 which extends from the body 202.

Referring to FIG. 22A, the body 202 may include at least one lumen 208 extending therethrough sized to accommodate a guide wire 210, and an additional lumen 212 extending at least partially through the body 202 and sized to accommodate the support member 204. The body 202 is generally formed of a soft, flexible material.

In one preferred embodiment, the body 202 is formed of an extruded polymeric material, such as a polyether blocked amide or PEBA, commonly available under the trade name PEBAX. The body 202 is approximately 10 centimeters in length and has a distal section 214 which is necked down from a first larger diameter to a second smaller diameter at the distal end 216. Additionally, the distal end 216 may have a radius tip for atraumatic movement of the exchange device 200 and subsequent seating of the distal end 216 in the ostium of the vessel receiving treatment. The guide wire lumen 208 has an approximate diameter of 0.020 inches sized to accommodate guide wires having outside diameters of 0.018 inches and smaller. Support member 204 is inserted into the support lumen 212 and secured to the body 202 through an adhesive bond.

It is recognized that body 202 may take on alternative shapes and forms while remaining within the scope of the present invention. The body 202 could be a clip or a loop to provide controlled movement of support member 204 relative to guide wire 210 while still providing support to guide wire 210 located across the stenosis. For example, the body 202 may have a varying outside diameter as shown in FIG. 22A, or alternatively, as shown in FIG. 22B, may be formed of a uniform outside diameter. Although the length of body 202 may vary in accordance with the desired procedure, the length of body 202 is preferably between 10 and 30 centimeters.

In one preferred embodiment, the body 202 is formed by extruding a soft polymeric material over a wire mandrel to form guide wire lumen 208. Additionally, the polymeric material may be extruded over a partial mandrel to form the support member lumen 212 or the support member mandrel may be inserted into the extruded polymeric material before cooling. After cooling, the mandrels are removed and a lubricous coating is applied to the inner surface of guide wire lumen 208 and the outer surface of body 202. It is recognized that the outside diameter of body 202 may be varied by methods such as varying the amount of material deposited on the guide wire lumen mandrel or reheating and reforming the body 202 after cooling.

Support member 204 is inserted into support member lumen 212, and secured using an adhesive bond. In one preferred embodiment, the support member 204 is a wire-like member similar in length to guide wire 210. The support member 204 is formed of material similar to guide wire 210, but of a heavier construction relative to guide wire 210. Preferably, support member 204 is formed of 304SS, has a diameter of 0.038 inches or greater, and a length extending from body 202 of approximately 90 to 120 centimeters.

Support member 204 has an operative segment 220 which can be similar to the guide wire operative segment 52 previously disclosed in the specification and the guide wire operative segment disclosed in U.S. Pat. Ser. No. 08/369,190, filed on Jan. 5, 1995, entitled "Shaft Movement Control Apparatus and Method". The operative segment 220, along with a guide wire operative segment 222, cooperate with a captivation tool 224 to create a coupling force field between the operative segment 220, operative segment 222, and captivation tool 224 indicated in FIG. 22C. The captivation tool 224 can be similar to the captivation tool 50 having a magnetically active area as previously disclosed in the specification, including the alternative embodiments shown in FIGS. 18–20.

Figure 22C:
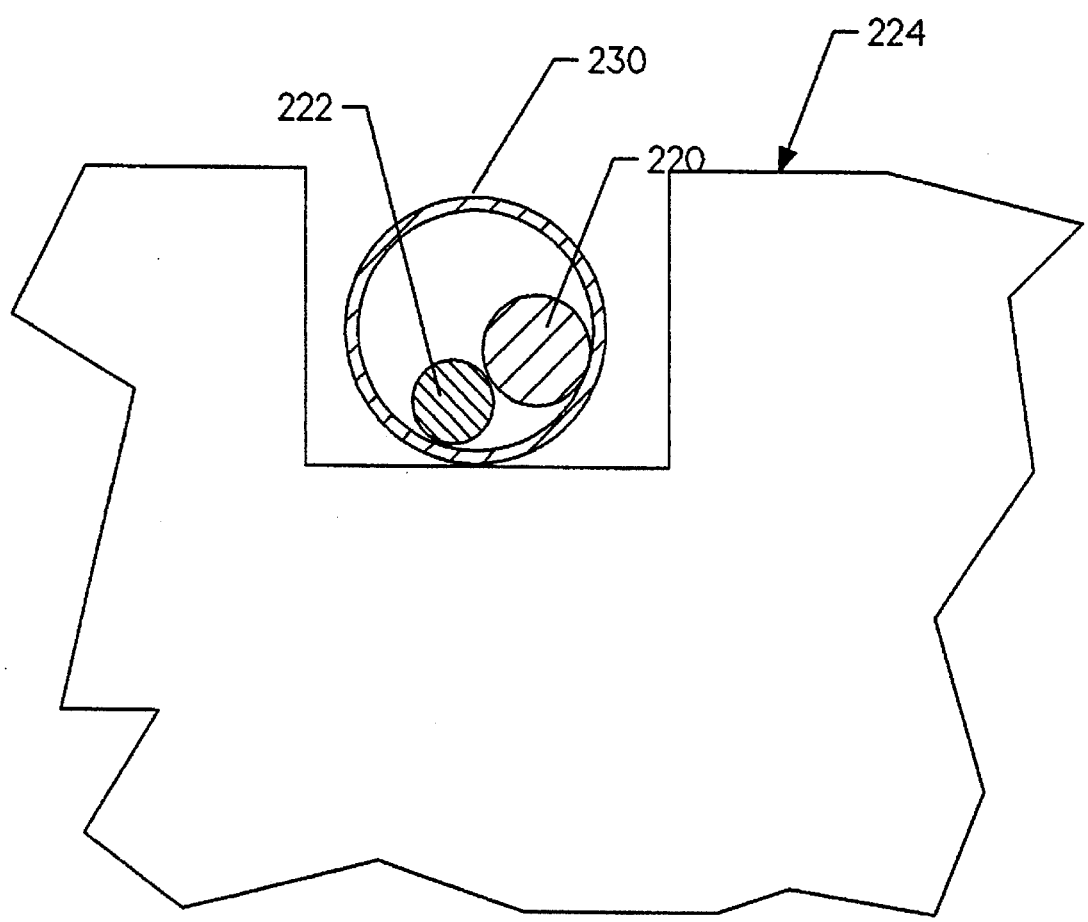
FIG. 22C is a cross-sectional view of the guide catheter exchange device shown in FIG. 22 operative segment positioned in a captivation tool.
Figure 22D:
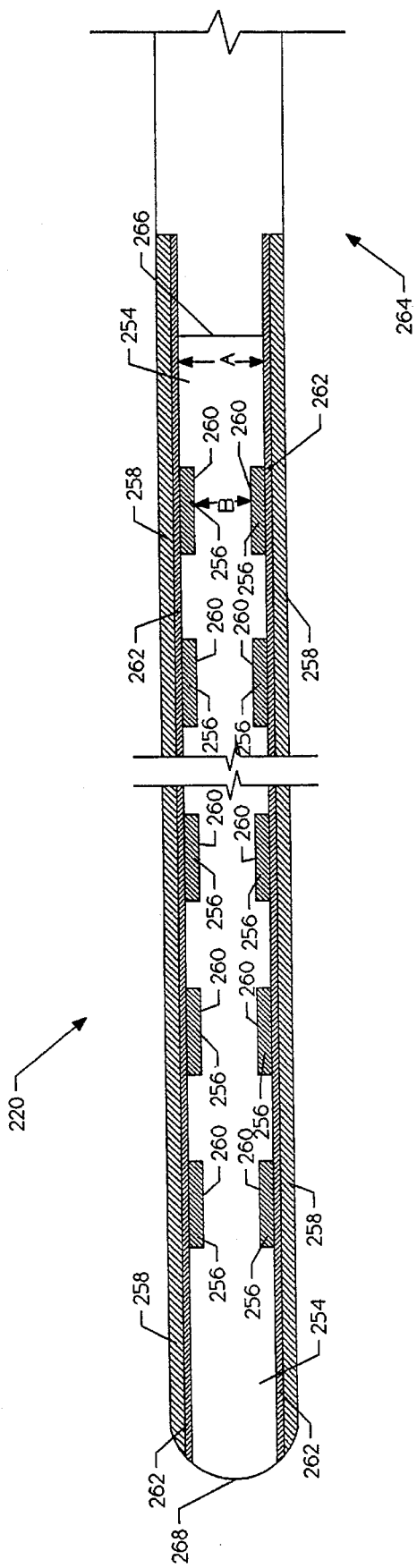
FIG. 22D is a partial cross-sectional view showing one alternative embodiment of the operative segment of the guide catheter exchange device of FIG. 22.

Referring to FIG. 22D, one preferred embodiment of operative segment 220 of support member 204 is shown in cross-sectional view. The operative segment 220 includes a core 254, segments 256, and a tubular member 258. Segments 256 are located within notched areas 260 of core 254. Tubular member 258 surrounds core 254, and has an outside diameter approximately equal to the outside diameter of the overall support member 204.

Core 254 is formed of a ferromagnetic material relative to the rest of operative segment 220, and becomes highly magnetic when subjected to a magnetic field. In a preferred embodiment, the core 254 is formed of a HYPERCO 50B, which is an alloy of approximately 48.5 percent cobalt, 48.5 percent iron, 3 percent Vanadium, and trace elements. It is also recognized that core 254 may be formed of other magnetically responsive or magnetically active materials, such as magnetic or paramagnetic materials.

In one embodiment, core 254 is formed by first pulling the HYPERCO material through a heated dye to form a HYPERCO wire or core. The HYPERCO wire is ground to a desired uniform outside dimension. Core 254 is notched in equally spaced areas longitudinally along the core 254. In one preferred embodiment, core 254 is notched by a centerless grinding process in which the HYPERCO wire is held longitudinally stationary while a wheel rotates while in contact with the wire for precision grinding each notch. In one embodiment, operative segment 220 includes approximately 180 notched segments 260 which are approximately 0.040 inches in length and 0.004 inches in depth. The longitudinal spacing of notched segment 160 are similar to the longitudinal spacing of the magnetically active segments in captivation tool 224.

Referring again to FIG. 22D, notched core 254 includes a larger major diameter A, and a smaller minor diameter B which together define the notched segments 260. A metallic or non-metallic substance is deposited within notched segments 260 to form segments 256. The substance occludes the space between the notched segments 260, such that core 254, including segments 256, is now formed of a uniform outer diameter equal to major diameter A. Segments 256 are formed of a metallic or nonmetallic substance which is non-magnetic or substantially less magnetic than the highly ferromagnetic core 254. The operative segment 220, including a core 254 having a plurality of metallic segments 256, results in a magnetic "edge" effect at each notched corner. This results in an operative segment having a very strong magnetic orientation in a direction longitudinal to the core 254, and a relatively weak magnetic attraction in a radial direction relative to the core 254.

A tubular member 258 is placed over core 254. In a preferred embodiment, the tubular member 258 is formed of a stainless steel hypotube having an outside diameter approximately equal to the outside diameter of the remaining portion of support member 204, and an inside diameter which is 0.0005 inches greater than the core 254 major diameter A. The tubular member 258 may be placed over core 254 while located in an adhesive bath for securing the tubular member 258 to the core 254. In a preferred embodiment, the adhesive bath is HYSOL adhesive, available from Dexter Company, which forms the adhesive layer 262 shown between tubular member 258 and core 254. Adhesive which forms around the outside diameter of tubular member 258 is subsequently removed.

Operative segment 220 is completed by center grinding the distal end 264 of operative segment 220 to compliment a ground portion of the proximal end of support member 204. Operative segment 220 is then securely attached to support member 204 by known means, such as a resistance weld, indicated at 266. Additionally, the proximal end 268 of operative segment 220 is ground smooth.

Figure 22E:
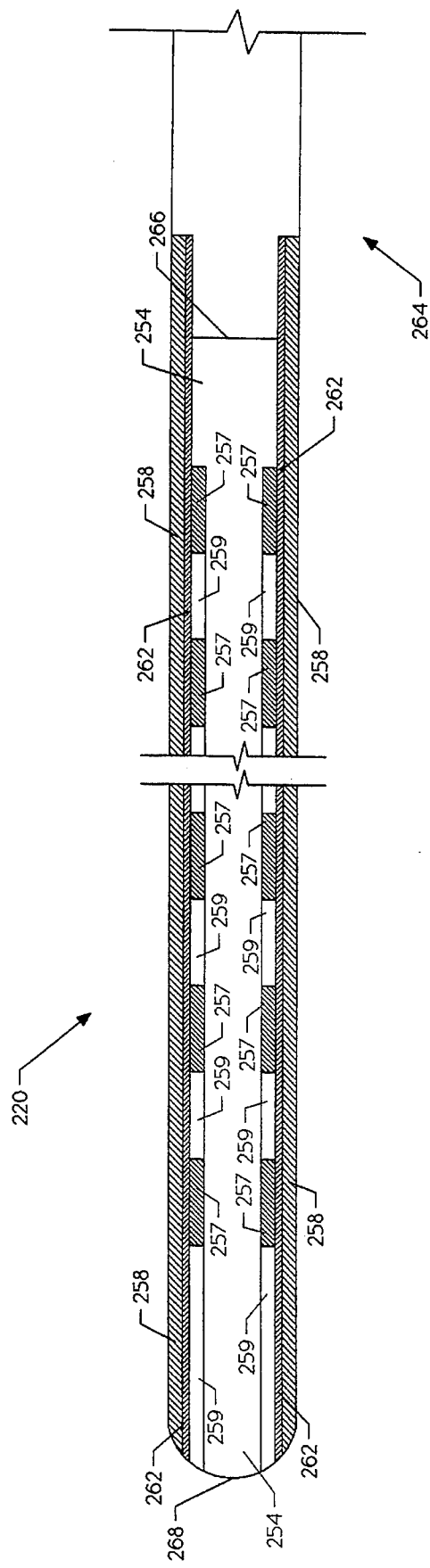
FIG. 22E is a partial cross-sectional view showing another alternative embodiment of the operative segment of the guide catheter exchange device of FIG. 22.

Referring to FIG. 22E, an alternative embodiment of operative segment 220 of support member 204 is shown in cross-sectional view. The operative segment 220 can be similar to the operative segment 220 shown in FIG. 22D. The operative segment 220 includes a core 254, ferromagnetic disks 257, and non-ferromagnetic disks 259. Core 254 is ground to a uniform outside diameter. Ferromagnetic disks 257 and non-ferromagnetic disks 259 are alternately placed over core 254. In the preferred embodiment, the ferromagnetic disks 257 are formed of HYPERCO. Similar to the embodiment shown in FIG. 22D, tubular member 258 is placed over ferromagnetic segments 257 and non-ferromagnetic segments 259. Tubular member 258 has an outside diameter approximately equal to the outside diameter of the overall support member 204.

Figure 22F:
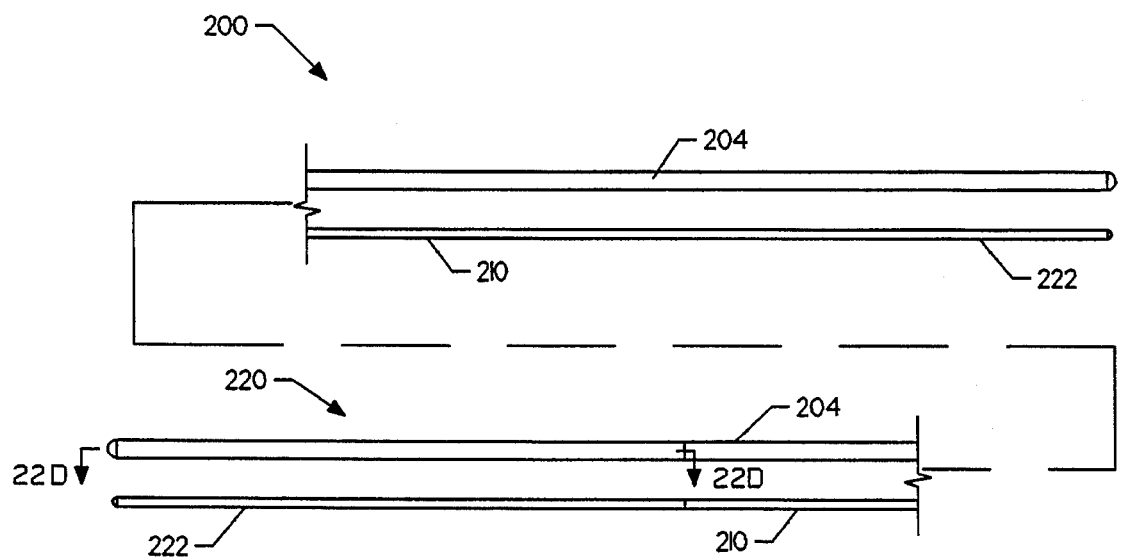
FIG. 22F is a perspective view of another embodiment of the guide catheter exchange device of the present invention.

Referring to FIG. 22F, it is recognized that in an alternative embodiment, the guide catheter exchange device 200 may include a support member 204 which does not include a body 202. In this embodiment, during a guide catheter exchange procedure, the support member 204 is positioned adjacent the guide wire 210. The guide wire 210 does not pass through the support member 204. Support member 204 provides the necessary support and stability for removing a guide catheter during the guide catheter exchange procedure, while providing protection to the guide wire 210, which is held in a stationary position across the stenosis. As with the embodiments of FIGS. 22D and 22E, the operative segment 220 of the support member can include ferromagnetic segments via core construction. In the alternative, the core can be formed of other magnetically responsive or magnetically active materials, such as magnetic or paramagnetic materials.

Figure 23E:
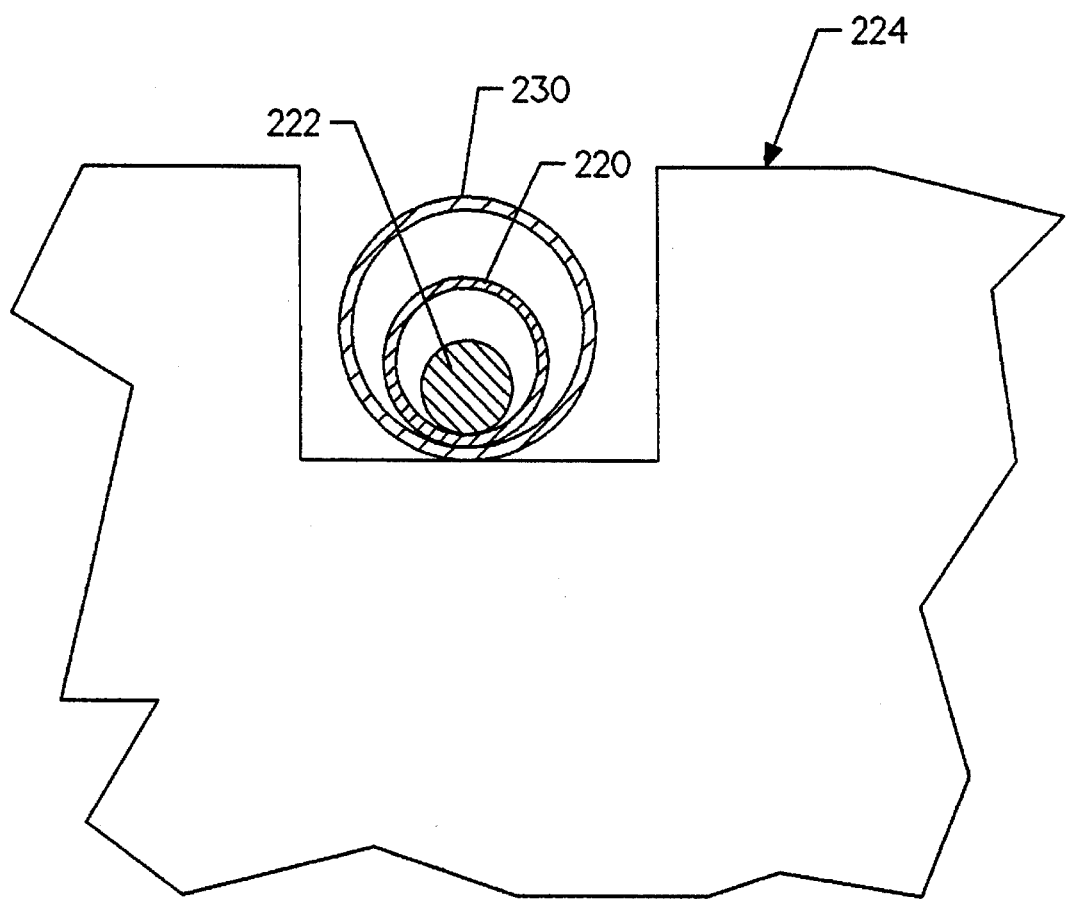
FIG. 23E is a cross-sectional view of the guide catheter exchange device of FIG. 23 operative segment located in a captivation tool.

Another embodiment of the guide catheter exchange device 200 is shown in FIG. 23. The guide catheter exchange device 200 includes a generally tubular shaped member 270 having a distal end 272, a proximal end 274 and a lumen 276 extending therethrough. The lumen 276 is sufficiently sized to allow guide wire 210 to pass through the lumen 276. During a guide catheter exchange procedure, guide catheter exchange device 200 may be positioned over guide wire 210, or alternatively as shown in FIG. 23G, guide catheter exchange device 200 may be positioned adjacent guide wire 210. Generally tubular shaped member 270 includes a tubular body 278 with an operative segment 220 located at its proximal end 274.

The distal end 272 of the guide catheter exchange device 200 allows for stabilization and protection of the guide wire 210, and structural support for the guide catheter during a guide catheter exchange procedure. The operative segment 220 located at the tubular member 270 proximal end 274 is formed integral the tubular shaped member 270. The operative segment 220 allows a physician to use the guide catheter exchange device 200 for performing a guide catheter exchange procedure by a solo physician without the need of exchange wires, while maintaining the position of the previously inserted guide wire across the stenotic lesion.

Tubular body 278 is formed from an extruded polymeric material through an extrusion process which may include extruding a polymeric material over a wire mandrel, or a free extrusion process. As previously described, the operative segment 220 is magnetically responsive for coupling to a captivation tool 224 indicated at FIG. 23E.

The generally tubular shaped member 270 may be formed of a uniform outside diameter, indicated in FIG. 23. Alternatively, tubular shaped member 270 may have a varying outside diameter as indicated in FIG. 23A where operative segment 220 is formed of a larger outside diameter relative to tubular body 278.

Referring to FIG. 23B, a cross-sectional view of the tubular shaped member 270 operative segment 220 is shown generally at 280. In one preferred embodiment, the tubular shaped member 270 operative segment 220 includes a base layer 282, a magnetically responsive layer 284, and an outside layer 286. In one embodiment, the base layer 282 is formed of an extruded polymeric material in a generally tubular shape. Magnetically responsive layer 284 is formed by wrapping or braiding wire or ribbon 288 around base layer 282.

In one embodiment, magnetically responsive layer 284 is formed of a highly ferromagnetic material, such as HYPERCO ribbon. In one preferred embodiment, the magnetically responsive layer 284 includes a first layer 290 and a second layer 292. The first layer 290 is formed by coiling 0.002 inch by 0.004 inch HYPERCO ribbon about the base layer 282. The second layer 292 is formed by intermittently coiling a similar 0.002 inch by 0.004 inch HYPERCO ribbon around the previously coiled first layer 290, with a spacing between the intermittent coils of approximately 0.02 inches, indicated at A, matching the segmented active area of captivation tool 224. The coiled layer 284 configuration including the size and spacing of the first layer 290 and second layer 292, are chosen to maximize the longitudinal attractive force between the captivation tool 224 and operative segment 220, while minimizing the radial attractive force between captivation tool 224 and operative segment 220. A smooth outer surface is provided to operative segment 220 by outside layer 286, where a soft polymeric material is extruded over the coiled layer 284. Additionally, a soft, rounded end 294 may be secured to the operative segment 220 by known methods, such as heat welding.

Referring to FIG. 23C, an alternative embodiment of the operative segment 220 shown in FIG. 23 is indicated generally at 296. The operative segment 220 includes a generally tubular member 298 formed of a polymeric material, such as PEBA, with cores 300 located within cavities 302 integral the tubular member 298. The cores 300 are preferably formed of a highly paramagnetic, ferromagnetic, or magnetic material. In one embodiment, the cores 300 are formed of notched HYPERCO.

The operative segment 220 may be formed by extruding tubular member 298 over a wire mandrel, and inserting core pins 300 within the tubular member 298 before cooling. Alternatively, operative segment 220 may be formed by first extruding a polymeric material over a wire mandrel to form tubular member 298, including smaller mandrels to form cavities 302. Core pins 300 are then inserted into cavities 302 and attached by adhesive. Additionally, a smooth end 304 may be attached to operative segment 220.

Figure 23F:
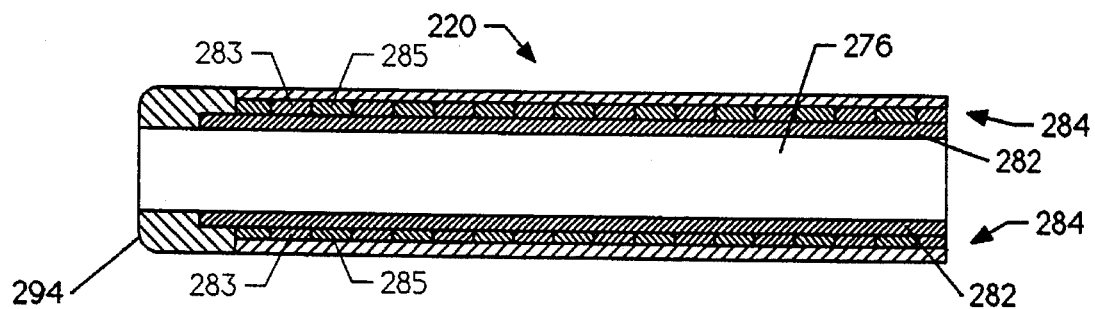
FIG. 23F is a partial sectional view of an alternative embodiment of the operative segment shown in FIG. 23.

Referring to FIG. 23F, an alternative embodiment of the operative segment 220 shown in FIG. 23 is shown. The operative segment 220 includes a generally tubular base layer 282 formed of an extruded polymeric material in a generally tubular shape. Magnetically responsive layer 284 is formed by alternately positioning ferromagnetic disks 283 and non-ferromagnetic disks 285 over the base layer 282. Although only a small number of disks 283 and 285 are shown, it is recognized that the size and number of disks may be varied to achieve a desired length for operative segment 220. Additionally, the width of disks 283 and 285 may be formed to match the magnetically active segments of the captivation tool 224. Similar to FIG. 23B, an outside layer 286 may be extruded over the disks 283 and 285, and a soft rounded end 294 may be secured to operative segment 220.

It is recognized that generally tubular shaped member 270 may include a single lumen extending therethrough, or alteratively, may be formed including a multi-lumen catheter member. The operative segment 220 active areas may be formed around, or encircle, the single or multi-lumens, as shown in FIGS. 23, 23A, 23B, 23C, and 23D, or the active area may be located adjacent the lumen extending therethrough as shown in FIG. 24.

Referring now to FIG. 23G, it is recognized that in an alternative embodiment, the guide catheter exchange device of FIG. 23 can be utilized without placing the guide wire 210 through the lumen 276 thereof. With this embodiment, the exchange is accomplished by placing the guide catheter exchange device 200 along side of the guide wire 210 within the lumen of the guide catheter to be exchanged. As with the other embodiments disclosed above, the operative segment 220 of the guide catheter exchange device 200 can include ferromagnetic segments, or in the alternative, can be formed of other magnetically responsive or magnetically active materials such as magnetic or paramagnetic materials.

Referring to FIG. 24, yet another alternative embodiment of the generally tubular shaped member 270 having an operative segment 220 is shown generally at 310. The operative segment 220 is shown in cross-sectional view in FIG. 24A. Operative segment 220 includes a guide wire lumen 208 and a magnetically active core 314 located within a soft, flexible layer 312.

The operative segment 220 is formed by simultaneous extrusion of a soft polymeric material over a wire mandrel (to form guide wire lumen 208) and magnetically active core 314. Alternatively, a first layer of polymeric material may be extruded over a mandrel forming guide wire lumen 208; and after cooling, the magnetically active core 314 may be placed next to the extruded mandrel, and a second extrusion layer is extruded over both the core 314 and extruded mandrel.

Core 314 is formed of a magnetically active or magnetically responsive material which preferably may be highly paramagnetic, ferromagnetic or magnetic. In one preferred embodiment, core 314 is formed of a notched HYPERCO wire. It is recognized that operative segment 220 may take on many different shapes and sizes. In one embodiment, the size of core 314 may be similar to the size of guide wire lumen 208, or alternatively, core 314 may be larger relative to guide wire lumen 208.

The guide catheter exchange device 200 of the present invention, indicated in FIGS. 22–24, allows a guide catheter exchange procedure to be performed by a solo physician without requiring an exchange wire, an extension wire, or additional intravascular devices to accomplish a guide catheter exchange procedure over the guide wire 210 while maintaining the position of the guide wire across the stenosis. It is desirable to hold the guide wire 210 and place it across the stenosis during a guide catheter exchange procedure to eliminate the need to reestablish the position of the guide wire 210 by retracing the tortuous path to the stenosis after the guide catheter is exchanged. Maintaining the guide wire 210 in place after an initial dilatation also provides the physician with a path through the stenosis in case of an abrupt closure of the vessel.

In one preferred embodiment of the present invention, captivation tool 224 cooperates with operative segment 220 of the guide catheter exchange device 200, and an operative segment 222 of the guide wire 210, to create a coupling force field between the captivation tool 224, the operative segment 220 and operative segment 222. The coupling force field is defined by an energy field (such as a magnetic field). The force generated by the field is strong enough to maintain the position of the guide catheter exchange device 200 and guide wire 210 relative to the captivation tool 224 when the guide catheter is aligned over the operative segments 220 and 222, and particularly when the guide catheter is moved over the guide wire 210 and guide catheter exchange device 200.

Figure 25:
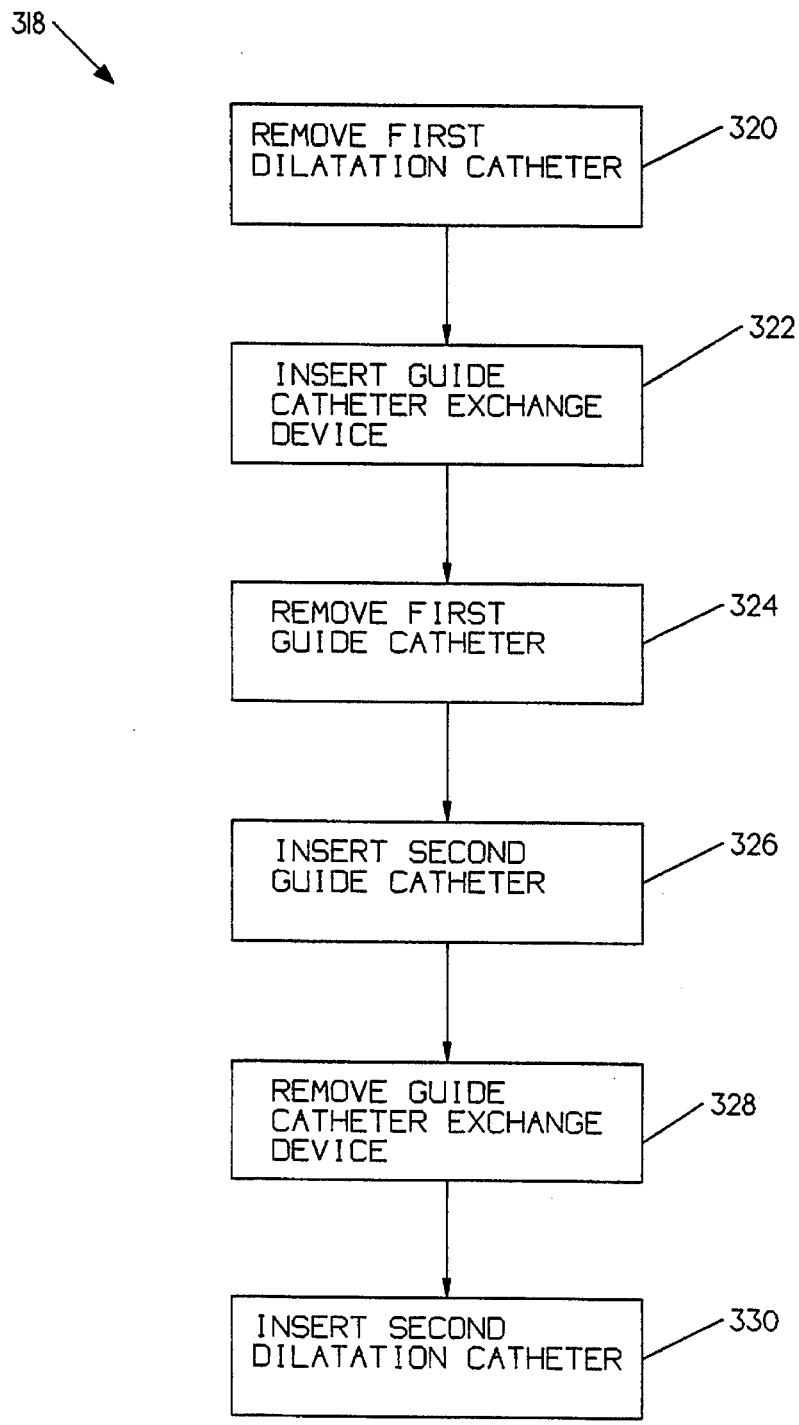
FIG. 25 is a flow diagram of a guide catheter exchange procedure using the guide catheter exchange device of the present invention.

Referring to FIG. 25, a physician may desire to perform a guide catheter exchange procedure after a dilatation catheter system has been located within a patient's vascular system. A guide catheter exchange method flow diagram is shown generally at 318. The dilatation catheter is first removed using the procedure previously described within this specification indicated at 320. In summary, the physician grasps the proximal end of the guide wire 210 to maintain its distal end in place across the stenosis. The physician then places the guide wire operative segment 222 into the slot of the captivation tool 224. The guide wire operative segment 222 is attracted to the magnetic sections of captivation tool 224 by the resultant magnetic field created therebetween. This results in the guide wire 210 being pulled against the bottom surface of the captivation tool 224.

The physician may now proceed with removal of the dilatation catheter by pulling the dilatation catheter proximally over the guide wire 210 and past captivation tool 224, while holding the captivation tool 224 in a stationary position relative to the patient outside of the guide catheter. The dilatation catheter is pulled over the guide wire 210 while maintaining the guide wire 210 in the same position relative to the captivation tool 224, and correspondingly maintaining the guide wire 210 in position across the stenosis. The physician then separates the guide wire 210 from the captivation tool 224.

The guide catheter exchange device may now be inserted, indicated at 322. While holding the guide wire 210 stationary relative to the patient, the guide catheter exchange device 200 is placed on the proximal end of the guide wire 210 and moved distally over the guide wire 210 until the guide wire operative segment 222 of the guide wire 210 is positioned just distal to the distal end of the guide catheter exchange device 200. The guide wire operative segment 222 is then positioned within captivation tool 224, through guide catheter 230, and brought into magnetic alignment. The physician then releases the guide wire 210, grasps the guide catheter exchange device 200, and distally advances the guide catheter exchange device 200 over the guide wire 210 longitudinally relative to captivation tool 224 and the guide wire 210 to distally advance the guide catheter exchange device through the guide catheter 230. Alternatively, the guide catheter exchange device 200 may be positioned within a patient's vascular system adjacent the guide wire 210.

During the guide catheter exchange device 200 advancement, the captivation tool 224 is held stationary relative to the patient to ultimately maintain the distal end of the guide wire 210 in place across the stenosis. The guide catheter exchange device 200 is advanced distally over the guide wire 210 until the operative segment 220 of the guide catheter exchange device 200 is located just proximal to the captivation tool 224. The magnet is released and the guide catheter exchange device 200 is advanced until operative segment 220 and guide wire 210 align by holding the guide wire proximal.

The first guide catheter 230 may now be removed. If the captivation tool 224 is attached to guide catheter 230, it is released before guide catheter 230 removal. Holding the captivation tool 224 in one hand, the physician then grasps the proximal end of the guide catheter 230 proximally of the captivation tool 224. The guide catheter 230 is pulled proximally over the guide wire 210 and guide catheter exchange device 200 while holding the tool 224 in a stationary position relative to the patient. The physician may choose to hold the tool 224 in his hand, or alternatively, the physician may place the tool 224 on the table or in a docking station to hold the tool 224 stationary.

The guide catheter 230 is pulled over the guide wire 210 and guide catheter exchange device 200 while maintaining guide wire 210 and guide catheter exchange device 200 stationary relative to the captivation tool 224 and the patient's body. The guide catheter 230 is withdrawn until the distal end of the guide catheter 230 is exposed outside of the patient's body. As such, a portion of the guide catheter exchange device 200 will be exposed between the distal end of the guide catheter 230 and the patient's body. The physician then grasps this exposed portion of the guide catheter exchange device 200, and separates it from the captivation tool 224 overcoming the radial magnetic forces between the guide catheter exchange device 200, guide wire 210, and captivation tool 224. The physician then completely withdraws the guide catheter 230 proximally off of the guide catheter exchange device 200.

The second guide catheter 232 may now be inserted, indicated at 326. While maintaining the guide catheter exchange device 200 and guide wire 210 stationary relative to the patient, a second guide catheter 232 is placed on the proximal end of the guide catheter exchange device 200 and guide wire 210 and moved distally over the guide catheter exchange device 200 and guide wire 210 until the operative segments 220 and 222 are positioned just distal to the distal end of the second guide catheter 232.

The guide catheter exchange device operative segment 220 and the guide wire operative segment 222 are placed within the captivation tool 224. The physician then releases the guide catheter exchange device 200 distally of the captivation tool 224, grasps the second guide catheter 232, and distally advances the second guide catheter 232 over the guide catheter exchange device 200 and guide wire 210 longitudinally relative to captivation tool 224 to distally advance the second guide catheter 232 through the patient's vascular system.

During guide catheter advancement, the captivation tool 224 is held stationary relative to the patient to ultimately maintain the distal end of the guide wire 210 stationary across the stenosis. The second guide catheter 232 is advanced distally over the guide catheter exchange device 200 until the proximal end of the guide catheter exchange device 200 and guide wire 210 extend beyond the proximal end of the second guide catheter 232.

The physician then grasps the guide catheter exchange device 200 and guide wire 210 proximal to the captivation tool 224 and second guide catheter, and separates the second guide catheter and the guide catheter exchange device 200 and guide wire 210 within the captivation tool 224. The second guide catheter is then further advanced distally over the guide catheter exchange device 200 until it reaches a desired location near the stenosis to be treated.

The guide catheter exchange device 200 is then removed from the patient's body indicated at 328. The guide wire operative segment 222 is positioned within captivation tool 224 after the guide catheter exchange device operative segment 220 has been moved proximal to captivation tool 224. The proximal end of guide catheter exchange device 200 is pulled proximally over the guide wire 210, while holding captivation tool 224 stationary to maintain the position of guide wire 210 across the stenosis. The guide catheter exchange device 200 is pulled distally until the distal end of the guide catheter exchange device 200 is removed from the patient's body. The physician then grasps the guide wire 210 at a location between the body and the distal end of guide catheter exchange device 200, and removes the remaining portion of the guide catheter exchange device 200 from the guide wire 210.

A second dilatation catheter may now be inserted, indicated at 330. While still grasping the guide wire 210, a second dilatation catheter is placed on the proximal end of guide wire 210 and moved distally over the guide wire 210 until the guide wire operative segment 222 of the guide wire 210 is positioned within a distal end of the second dilatation catheter. The guide wire operative segment 222 is magnetically aligned with the magnetic sections of the captivation tool 224 outside of the guide catheter 232. The physician then releases the guide wire 210 distally of the captivation tool 224, grasps the second dilatation catheter, and distally advances the second dilatation catheter over the guide wire 210 longitudinally relative to captivation tool 224 and the guide wire 210 to distally advance the second dilatation catheter through the second guide catheter 232.

During the second dilatation catheter advancement, the captivation tool 224 is held stationary relative to the patient to ultimately maintain the distal end of the guide wire 210 in place across the stenosis. The second dilatation catheter is advanced distally over the guide wire 210 until the proximal end of the guide wire 210 extends beyond a proximal end of the second dilatation catheter. The physician then grasps the guide wire 210 proximal to the captivation tool 224 and dilatation catheter manifold, and separates the second dilatation catheter and the guide wire 210 therein from the captivation tool 224. The second dilatation catheter is then further advanced distally over the guide wire 210 until the balloon of the second dilatation catheter is positioned across the stenosis for dilatation.

The guide catheter exchange device 200 is used to perform guide catheter exchange procedures, while maintaining the position of the guide wire 210 relative to the stenosis. The present invention is ideally suited for facilitating guide catheter exchanges without the need for a long exchange guide wire, a modified guide catheter, or additional intravascular devices. The present invention allows guide catheter exchanges over a standard length guide wire using a guide catheter having a full length lumen. Additionally, the procedure may be performed by a single physician and without the prolonged use of x-ray fluoroscopy used to observe the position of the guide wire 210, since the guide wire 210 is held stationary by use of the present invention, and thus, its position need not be continuously observed.

It is recognized that the guide catheter exchange device 200 of the present invention having an operative segment 220 may be used with other dilatation catheter exchange procedures which do not employ the use of a guide wire having a magnetically active segment at its proximal end. For example, other methods may be employed to remove the balloon dilatation catheter during the guide catheter exchange procedure, such as guide wire extensions, rapid exchange catheter systems, over-the-wire and single operator exchange procedures.

It is recognized that the guide catheter exchange device of the present invention may be located adjacent the guide wire or be positioned over the guide wire during a guide catheter exchange procedure, while protecting the guide wire and providing support and stability during the guide catheter exchange procedure. Additionally, operative segment 220 may be provided on a short guide catheter exchange device extension. The short extension would connect to the proximal end of a larger guide wire to form a support member similar to the support member shown in FIG. 22F, or similarly may be a tubular shaped guide wire extension which is securely attached to a tubular member to form a guide wire exchange device as shown in FIG. 23.

Although the present invention has been described with reference to preferred embodiments, workers skilled in the art will recognize that changes may be made in form and detail without departing from the spirit and scope of the invention.

What is claimed:

1. A device for use in exchanging a first guide catheter for a second guide catheter, the device comprising:

a. a support member insertable within the first guide catheter, having a proximal end and a distal end; and b. means for coupling responsive to a magnetic source, carried by the support member, wherein the means for coupling maintains the support member stationary relative to a guide wire while exchanging the first guide catheter for the second guide catheter.

2. The device of claim 1, wherein the means for coupling includes a magnetically active segment located on the proximal end of the support member.

3. The device of claim 2, wherein the magnetically active segment includes a plurality of alternating ferromagnetic and non-ferromagnetic disks.

4. The device of claim 1, further including:

a. a magnetically active tool which, when positioned adjacent the magnetically active segment on the support means, couples the magnetically active segment to the magnetically active tool.

5. The device of claim 1, further wherein:

a. the support member includes a shaft having at least one lumen extending longitudinally therethrough, and further wherein the means for coupling responsive to a magnetic source includes a magnetically operative segment carried by the proximal portion of the shaft.

6. The device of claim 5, wherein the magnetically operative segment includes a magnetically responsive member which encircles the shaft lumen.

7. The device of claim 5, wherein the magnetically operative segment includes a magnetically responsive member located adjacent the shaft lumen.

8. The device of claim 1, further including:

a. a body having at least one lumen extending longitudinally therethrough fixedly secured to the distal end of the support member.

9. The device of claim 8, wherein the means for coupling responsive to a magnetic source includes a magnetically responsive segment carried on the proximal end of the support member.

10. The device of claim 9, wherein the magnetically responsive segment includes at least one notch.

11. A device for controlling the movement of a guide wire relative to a guide catheter, the device comprising:

a. a shaft having a proximal portion and a distal portion; and b. a magnetically operative segment carried by the proximal portion of the shaft, wherein the magnetically operative segment maintains the guide wire in a stationary position relative to the shaft during movement of the guide catheter.

12. The device of claim 11, wherein the magnetically operative segment includes at least one magnetically responsive member.

13. The device of claim 12, wherein the shaft includes at least one lumen extending longitudinally therethrough.

14. The device of claim 13, wherein the magnetically responsive member encircles the shaft lumen.

15. The device of claim 13, wherein the magnetically operative segment is located adjacent the shaft lumen.

16. The device of claim 13, wherein the magnetically operative segment includes at least one pin located adjacent the lumen.

17. The device of claim 13, wherein the magnetically operative segment includes at least one notch.

18. The device of claim 13, wherein the magnetically operative segment includes a coil.

19. The device of claim 13, wherein the magnetically operative segment includes a plurality of alternating ferromagnetic and non-ferromagnetic disks.

20. The device of claim 11, further including:
   a. a body secured to the distal end of the shaft having at least one lumen extending longitudinally therethrough.

21. The device of claim 20, wherein the body has a nonuniform outside diameter.

22. The device of claim 20, wherein the body further includes a soft tip.

23. The device of claim 20, wherein the magnetically operative segment includes a ferromagnetic core having at least one notch.

24. A method of maintaining position of a guide wire located within a patient's vascular system during exchange of a guide catheter, comprising the steps of:
   a. inserting an exchange device having a magnetically active segment at its proximal end within the guide catheter having a previously placed guide wire; and
   b. positioning the exchange device active segment within a magnetically active captivation tool.

25. The method of claim 24, further comprising the step of:
   a. moving the guide catheter relative to the exchange device.

26. A method for exchanging a guide catheter comprising the steps of:
   a. inserting an exchange device having a magnetically active segment at its proximal end within a guide catheter in a patient's vascular system, with a previously placed guide wire positioned within the guide catheter;
   b. removing the guide catheter over the exchange device;
   c. inserting a second guide catheter over the exchange device; and
   d. removing the exchange device.

27. The method of claim 26, further comprising the step of:
   positioning the exchange device active segment within a magnetically active captivation tool.

28. The method of claim 26, further comprising the step of:
   removing a balloon dilatation catheter system.

29. The method of claim 26, wherein the exchange device is inserted over the guide wire.

30. The method of claim 26, wherein the exchange device is positioned adjacent the guide wire.

31. The method of claim 26, wherein the exchange device includes a support member.

32. The method of claim 31, wherein the support member is generally tubular shaped.

33. The method of claim 31, wherein the support member includes a body having at least one lumen extending longitudinally therethrough located at the support member proximal end.

34. A method of protecting a guide wire during a guide catheter exchange procedure comprising the steps of:
   positioning an exchange device having a magnetically active segment with respect to a guide wire within a guide catheter in a patient's vascular system.

35. The method of claim 34, wherein the exchange device is positioned adjacent the guide wire.

36. The method of claim 34, wherein the exchange device is at least partially positioned over the guide wire.

* * * * *